United States Patent
Lynch et al.

(10) Patent No.: US 10,219,836 B2
(45) Date of Patent: Mar. 5, 2019

(54) ORTHOPEDIC EXTENDABLE RODS

(71) Applicant: GLOBUS MEDICAL, INC., Audubon, PA (US)

(72) Inventors: Bobby Lynch, Norristown, PA (US); Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/905,904

(22) Filed: Feb. 27, 2018

(65) Prior Publication Data
US 2018/0185069 A1  Jul. 5, 2018

Related U.S. Application Data

(63) Continuation of application No. 14/515,197, filed on Oct. 15, 2014, now Pat. No. 9,931,138.

(51) Int. Cl.
*A61B 17/70* (2006.01)

(52) U.S. Cl.
CPC ........ *A61B 17/7025* (2013.01); *A61B 17/702* (2013.01); *A61B 17/7017* (2013.01)

(58) Field of Classification Search
CPC .................................. A61B 17/7014–17/7017
See application file for complete search history.

(56) References Cited

U.S. PATENT DOCUMENTS

| | | | | |
|---|---|---|---|---|
| 4,931,055 A | * | 6/1990 | Bumpus | A61B 17/7014 606/254 |
| 5,466,261 A | * | 11/1995 | Richelsoph | A61F 2/36 606/60 |
| 6,106,525 A | * | 8/2000 | Sachse | A61B 17/8004 606/59 |
| 6,796,984 B2 | * | 9/2004 | Soubeiran | A61B 17/7216 606/246 |
| 7,942,908 B2 | | 5/2011 | Sacher et al. | |
| 8,092,499 B1 | * | 1/2012 | Roth | A61B 17/7004 606/254 |
| 8,287,596 B1 | * | 10/2012 | Heim | A61B 17/7074 606/279 |
| 9,060,810 B2 | * | 6/2015 | Kercher | A61B 17/7011 |
| 2006/0079897 A1 | * | 4/2006 | Harrison | A61B 17/66 63/900 |
| 2009/0076597 A1 | * | 3/2009 | Dahlgren | A61B 17/7016 623/2.1 |
| 2009/0204156 A1 | * | 8/2009 | McClintock | A61B 17/7002 606/278 |
| 2009/0281542 A1 | * | 11/2009 | Justis | A61B 17/7017 606/60 |
| 2010/0004697 A1 | | 1/2010 | Fortin et al. | |
| 2010/0114103 A1 | * | 5/2010 | Harrison | A61B 17/7016 606/90 |
| 2011/0137347 A1 | | 6/2011 | Hunziker | |

(Continued)

FOREIGN PATENT DOCUMENTS

| | | |
|---|---|---|
| KR | 100935233 B1 | 1/2010 |
| WO | 2009146377 A1 | 12/2009 |
| WO | 2013106262 A2 | 7/2013 |

*Primary Examiner* — Eduardo C Robert
*Assistant Examiner* — Michelle C Eckman

(57) ABSTRACT

Embodiments herein are generally directed to extendable rods for use in orthopedic assemblies. In some embodiments, these implants may be used in conjunction with procedures to treat spinal deformities, including, but not limited to, early onset scoliosis.

20 Claims, 15 Drawing Sheets

(56) References Cited

U.S. PATENT DOCUMENTS

| | | | |
|---|---|---|---|
| 2011/0196435 A1* | 8/2011 | Forsell | A61B 17/68 606/86 R |
| 2012/0271353 A1 | 10/2012 | Barry | |
| 2013/0338713 A1* | 12/2013 | Kawakami | A61B 17/7014 606/258 |
| 2015/0351805 A1* | 12/2015 | Miladi | A61B 17/7014 606/258 |
| 2016/0270825 A1* | 9/2016 | Wentz | A61B 17/7016 |
| 2018/0028235 A1* | 2/2018 | Simpson | A61B 17/7017 |

* cited by examiner

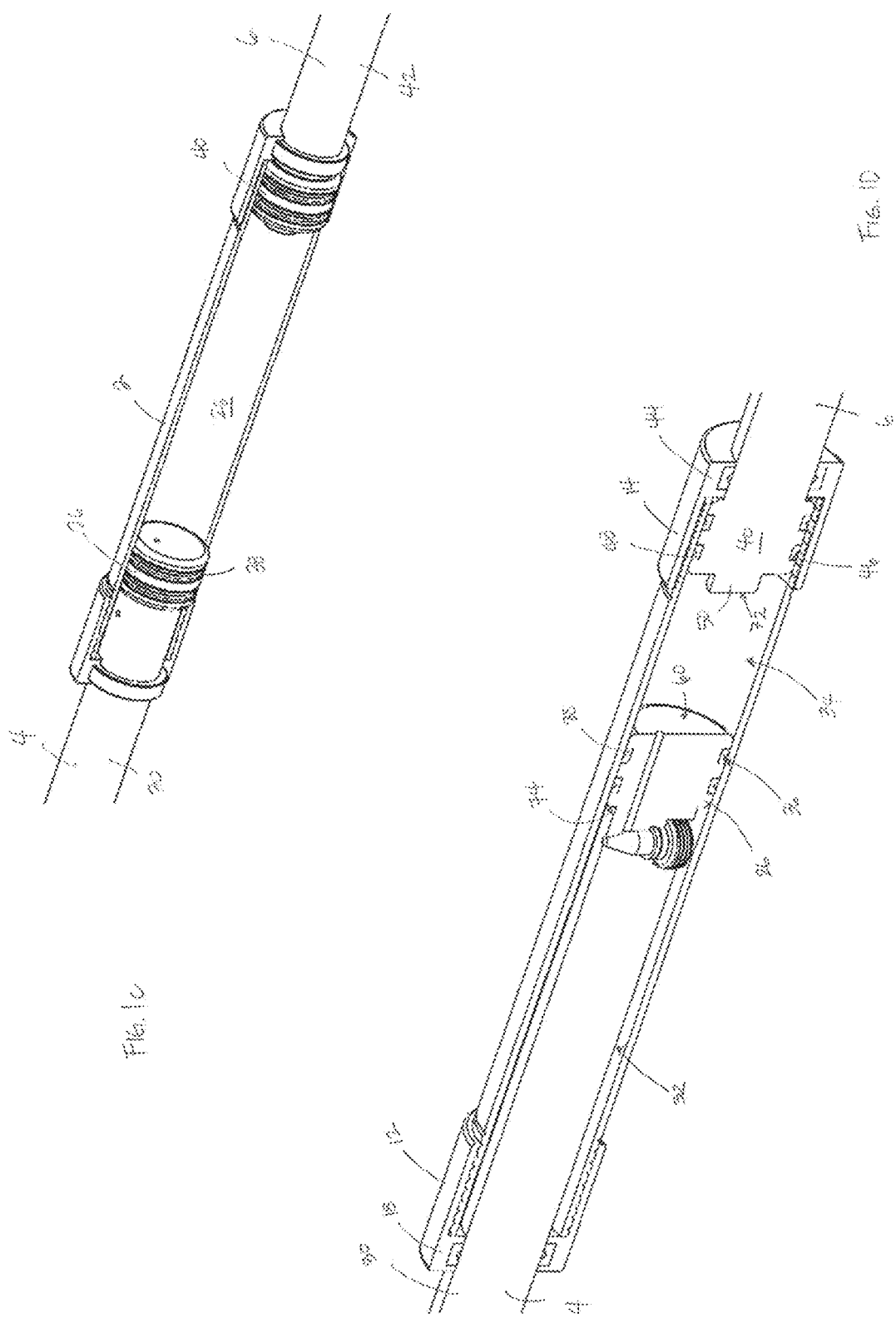

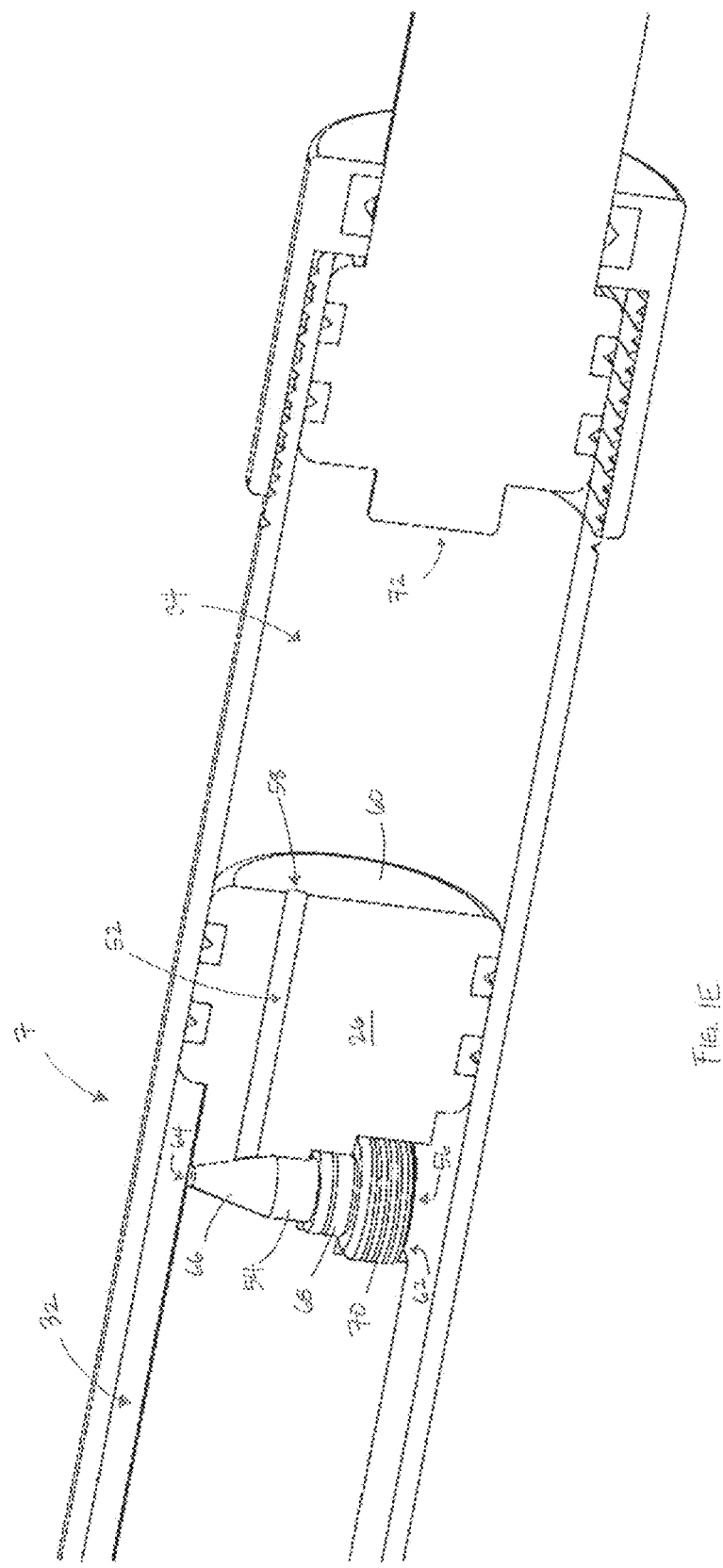

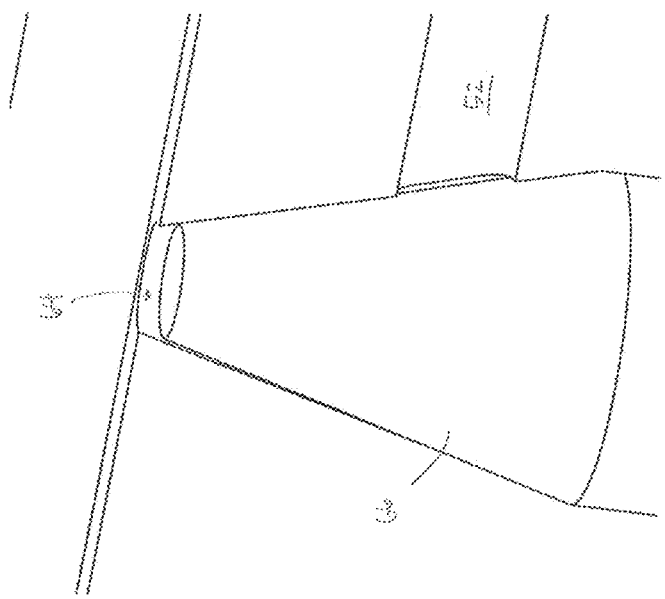
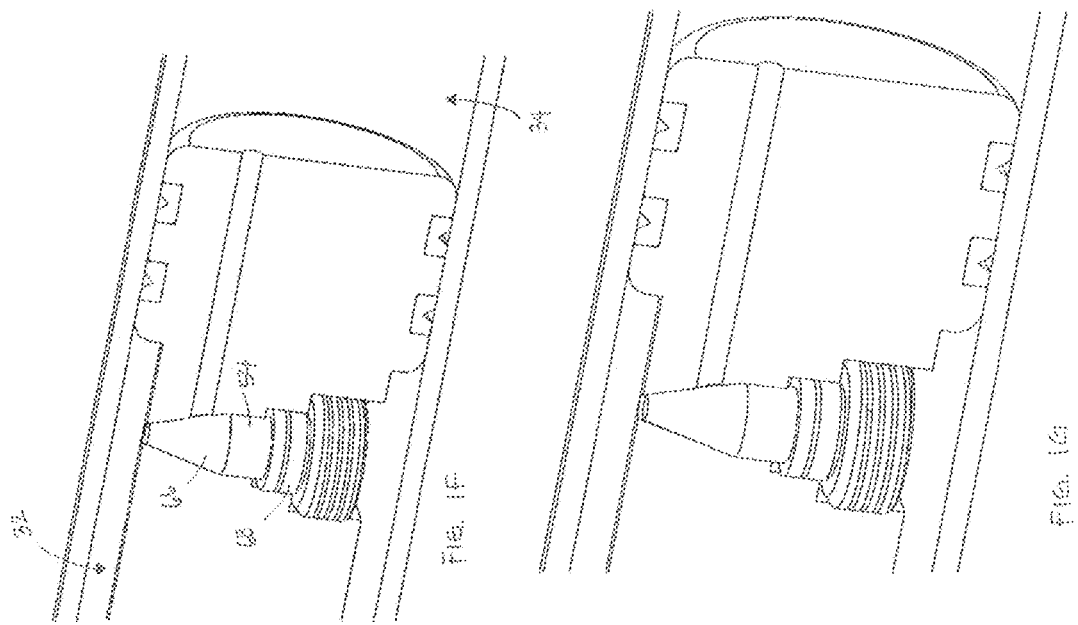

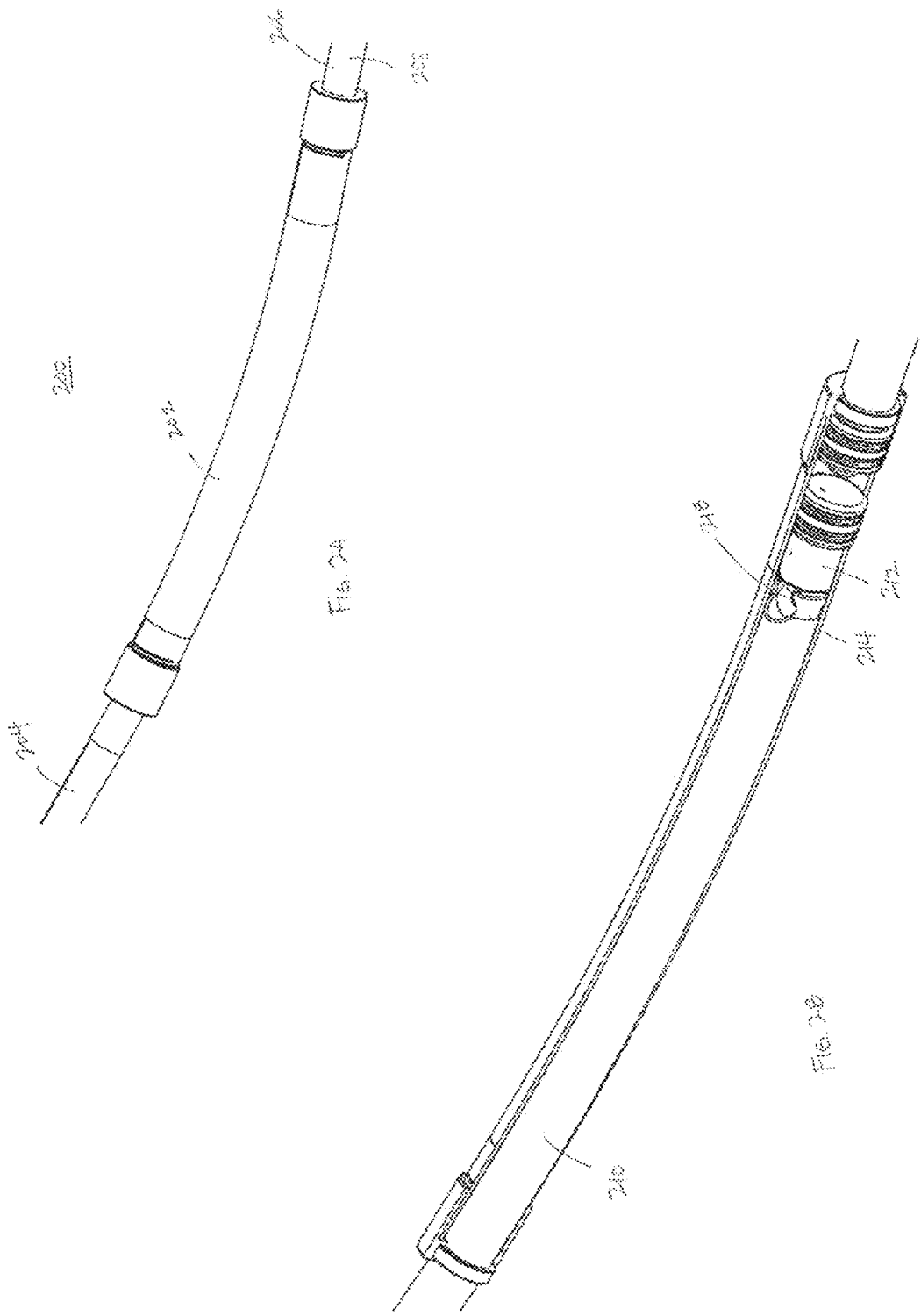

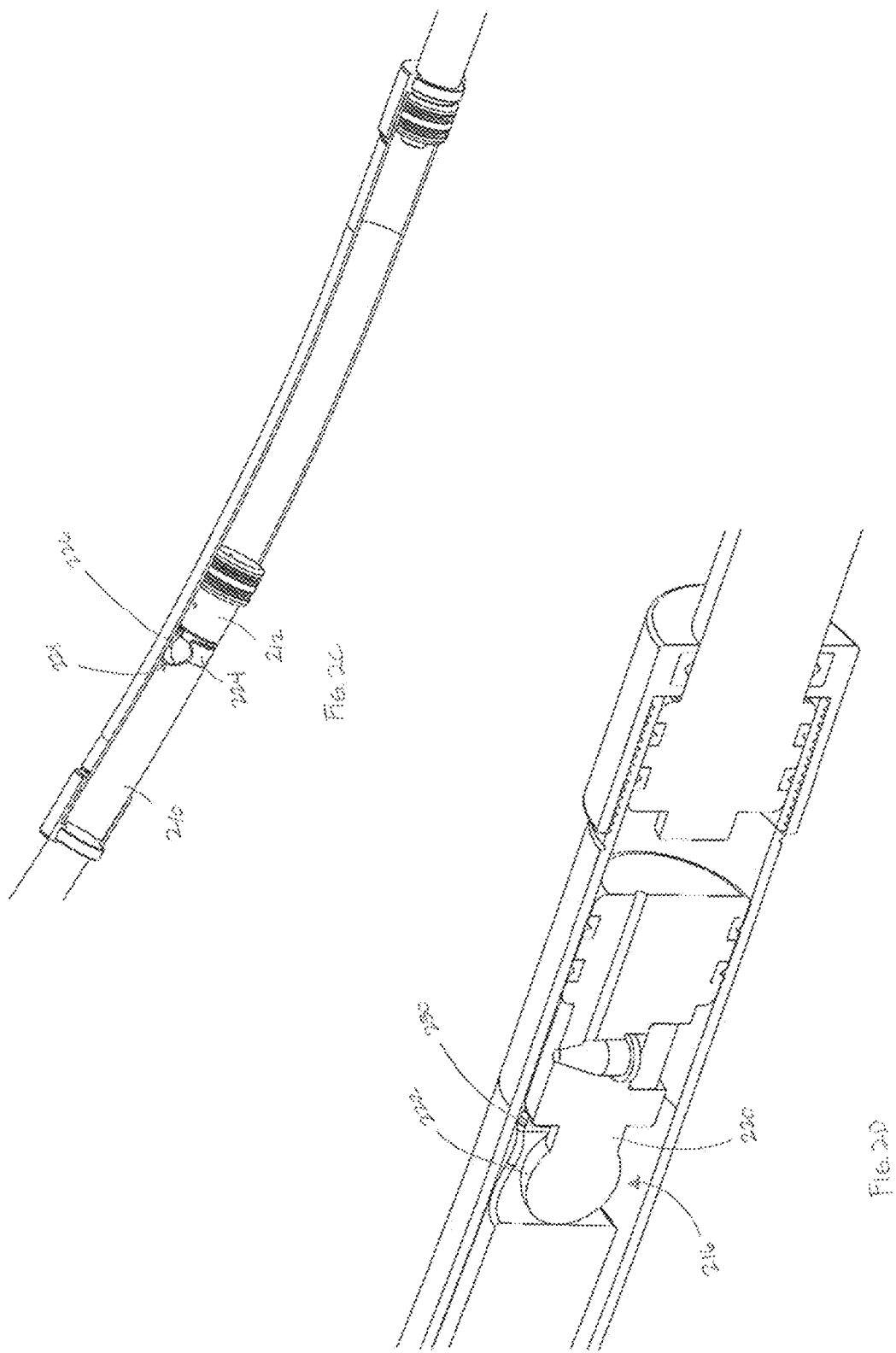

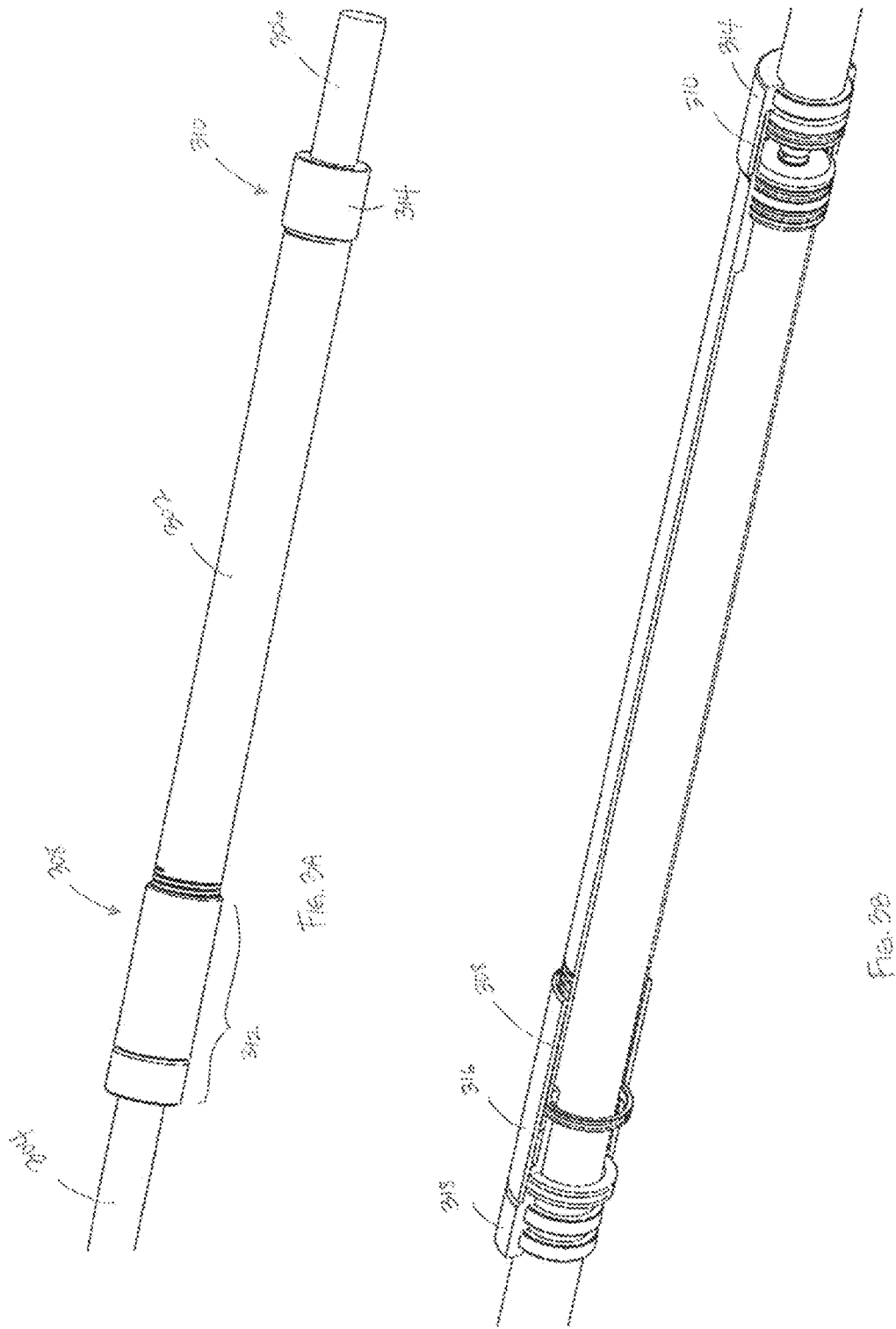

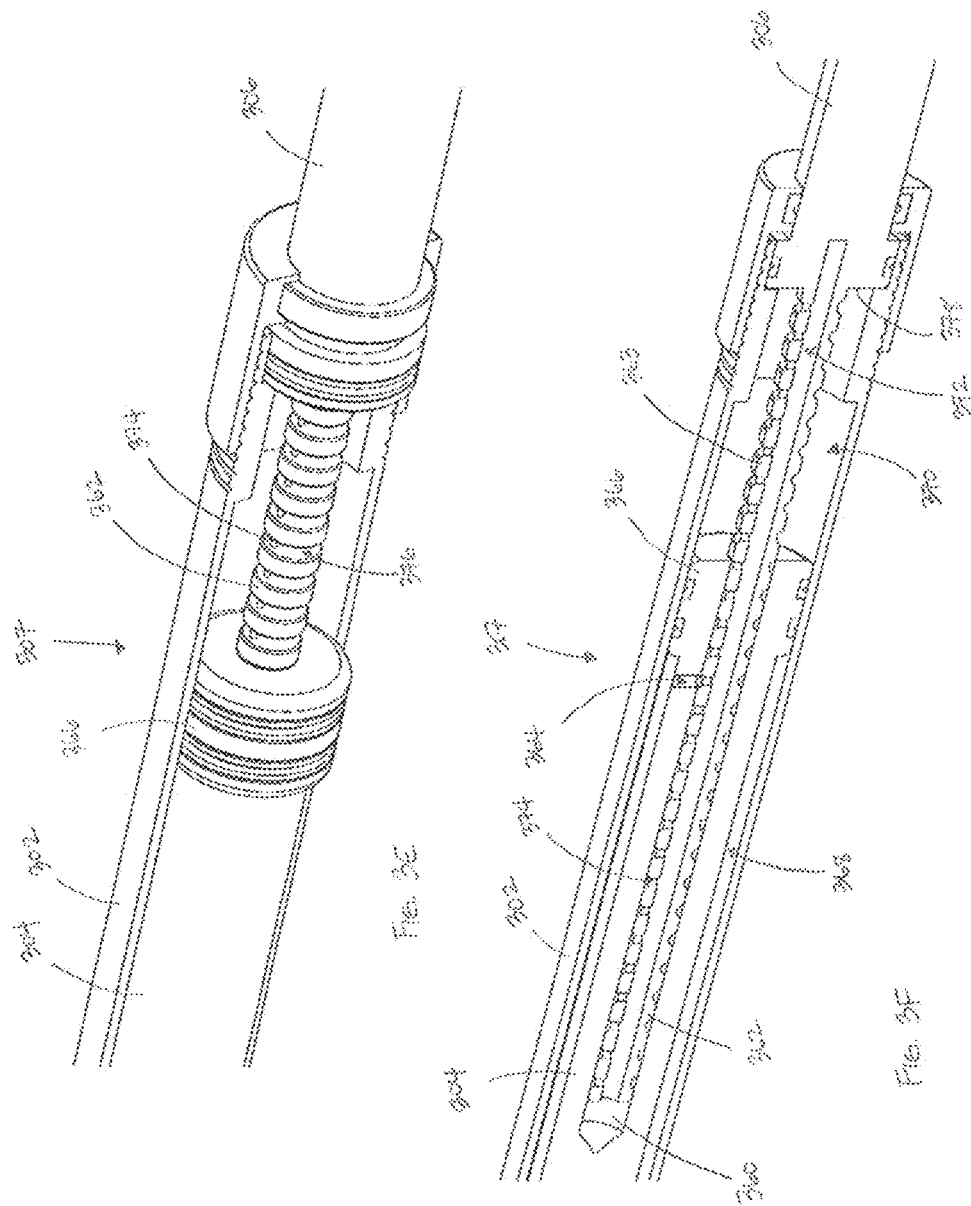

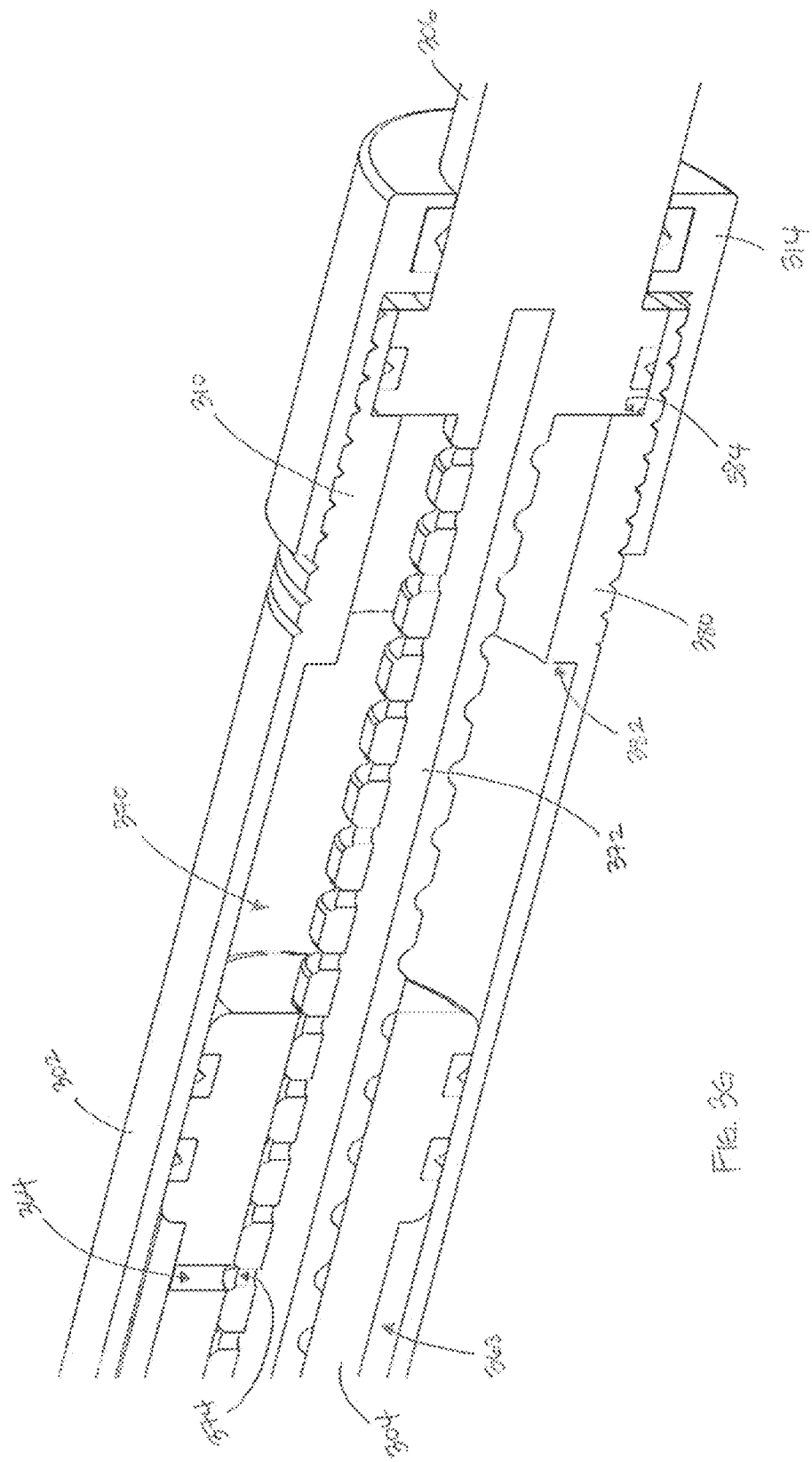

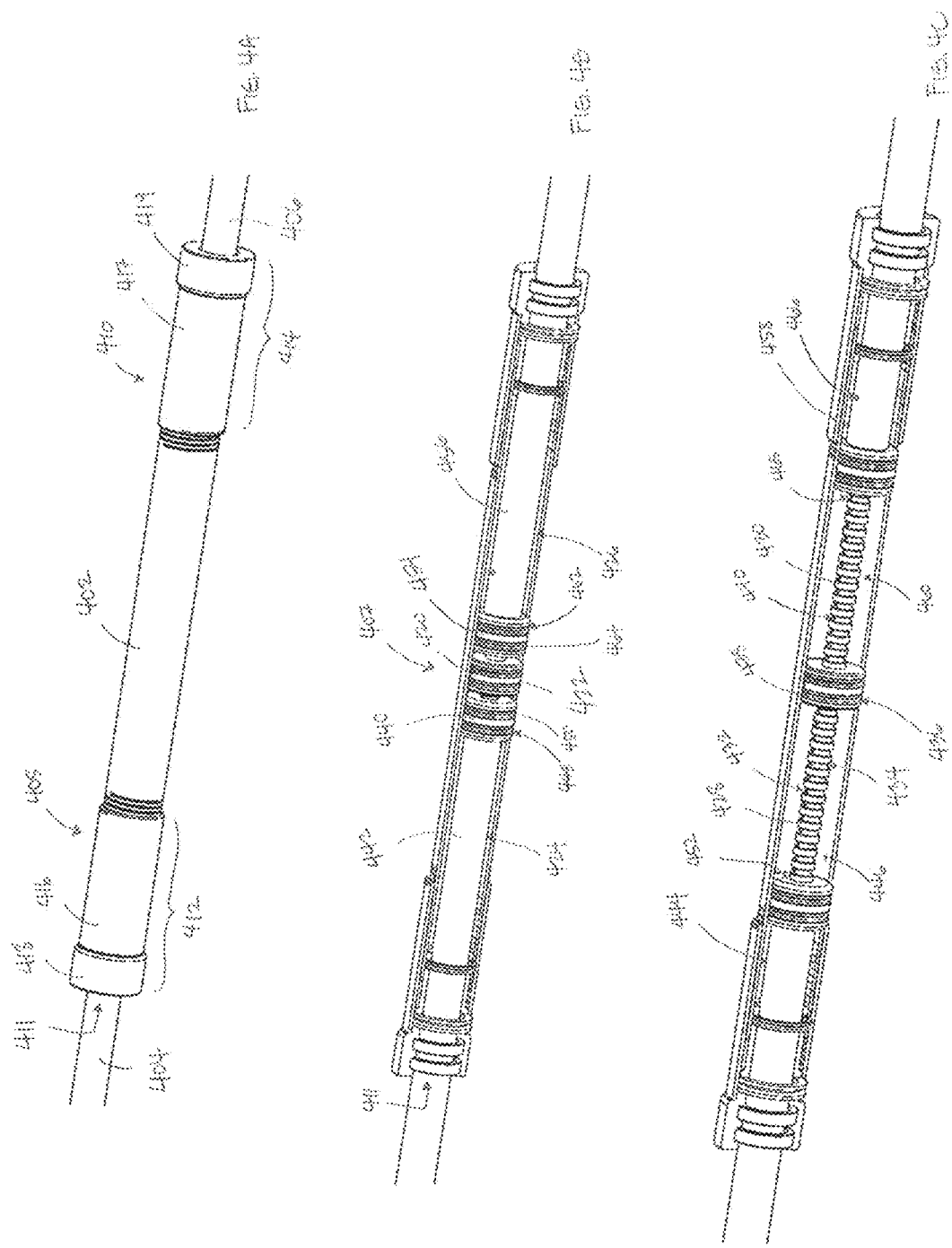

ORTHOPEDIC EXTENDABLE RODS

CROSS REFERENCE TO RELATED APPLICATIONS

This application is a continuation of U.S. patent application Ser. No. 14/515,197, titled "Orthopedic Expandable Rods," filed on Oct. 15, 2014, the entire disclosure of which is incorporated by reference herein in its entirety.

FIELD OF THE INVENTION

The present invention relates to orthopedic extendable rods and methods used to install and/or actuate these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One general example of a spinal irregularity is an abnormal curvature of the spine, for example, as exhibited with scoliosis, kyphosis, and/or lordosis. Scoliosis, a side-to-side curvature of the spine, can affect the dimensions of an individual's chest area, thereby impacting performance of internal organs such as the lungs and heart.

Treatment of scoliosis can include, for example, reducing the severity and preventing further progression of the irregularity through physical therapy, bracing, and/or surgery. Surgical procedures to treat scoliosis can include spinal fusion, wherein the vertebrae are straightened and one or more rods are placed along the spinal column to maintain the alignment.

SUMMARY OF THE INVENTION

Some embodiments herein are directed to an extendable rod assembly that can include an elongate sleeve comprising a cannula extending therethrough; an actuating rod comprising an enlarged head disposed within the cannula and a body extending in a first direction, wherein the enlarged head divides the cannula into a first chamber and a second chamber; a fixed rod comprising an enlarged head disposed within the cannula and a body extending in a second direction; and a valve assembly configured to control flow of a fluid between the first and second chambers.

Other embodiments herein are directed to an extendable rod assembly that can include an elongate sleeve comprising a cannula extending therethrough; a valve assembly comprising a valve body disposed within the cannula and comprising an enlarged head, wherein the enlarged head divides the cannula into a first chamber and a second chamber; a first actuating rod comprising a first enlarged head disposed within the first chamber and a body extending in a first direction, wherein the first enlarged head divides the first chamber into a first sub-chamber and a second sub-chamber; and a second actuating rod comprising a second enlarged head disposed within the second chamber and a body extending in a second direction, wherein the second enlarged head divides the second chamber into a third sub-chamber and a fourth sub-chamber; wherein the valve assembly is configured to control flow of a fluid between the first and second sub-chambers, and between the third and fourth sub-chambers.

Some embodiments herein are directed to an extendable rod assembly that can include an elongate sleeve comprising a cannula extending longitudinally therethrough and a port, wherein the port is configured to transfer a fluid in and out of the cannula; an actuating rod comprising a locking member, wherein at least a portion of the actuating rod is disposed within the cannula at a first end of the elongate sleeve; and a fixed rod comprising a head, wherein the head is disposed within cannula at a second end of the elongate sleeve.

Other embodiments herein are directed to a method of extending an extendable rod assembly, which can include providing an extendable rod assembly, wherein the extendable rod assembly has a first length; coupling the port with a fluid source; and introducing the fluid into the cannula; wherein the fluid causes the actuating rod to translate at least partially out of the cannula, thereby extending the extendable rod assembly to a second length that is greater than the first length.

Some embodiments herein are directed to an extendable rod assembly that can include an elongate sleeve comprising a conduit extending therethrough from a first end to a second end; an actuating rod comprising a plurality of gear teeth and at least partially disposed within the first end of the conduit; a fixed rod at least partially disposed within the second end of the conduit; and a gear assembly configured to actuate the actuating rod.

Other embodiments herein are directed to an extendable rod assembly that can include an elongate sleeve comprising a conduit extending therethrough and a housing member disposed thereon, wherein the housing member is in fluid communication with the conduit; a gear assembly mounted in the housing member; an actuating rod at least partially disposed within the conduit and extending in a first direction; and a fixed rod at least partially disposed within the conduit and extending in a second direction; wherein a member of the gear assembly is configured to directly engage the actuating rod.

Still other embodiments herein are directed to an elongate sleeve comprising a conduit extending therethrough, and further comprising a housing member in fluid communication with the conduit; a gear assembly disposed within the housing member; an actuating rod at least partially disposed within the conduit and extending in a first direction, the actuating rod comprising a plurality of teeth configured to mesh with a member of the gear assembly; and a fixed rod at least partially disposed within the conduit and extending in a second direction.

Yet other embodiments herein are directed to a method of extending an extendable rod assembly, which can include providing a extendable rod assembly having a first length, coupling a driver with a drive member of the extendable rod assembly, and applying torque to the drive member in a first direction to thereby extend the extendable rod assembly to a second length that is greater than the first length.

Further areas of applicability of the present disclosure will become apparent from the detailed description provided hereinafter. It should be understood that the detailed description and specific examples, while indicating certain embodiments, are intended for purposes of illustration only and are not intended to limit the scope of the disclosure.

BRIEF DESCRIPTION OF THE DRAWINGS

The present invention will become more fully understood from the detailed description and the accompanying drawings, wherein:

FIGS. 1A-H illustrate perspective and partial cross-sectional views of an extendable rod assembly as described herein;

FIGS. 2A-D illustrate perspective and partial cross-sectional views of an extendable rod assembly as described herein;

FIGS. 3A-G illustrate perspective and partial cross-sectional views of an extendable rod assembly as described herein;

FIGS. 4A-C illustrate perspective and partial cross-sectional views of an extendable rod assembly as described herein;

DETAILED DESCRIPTION

Figure 3C:
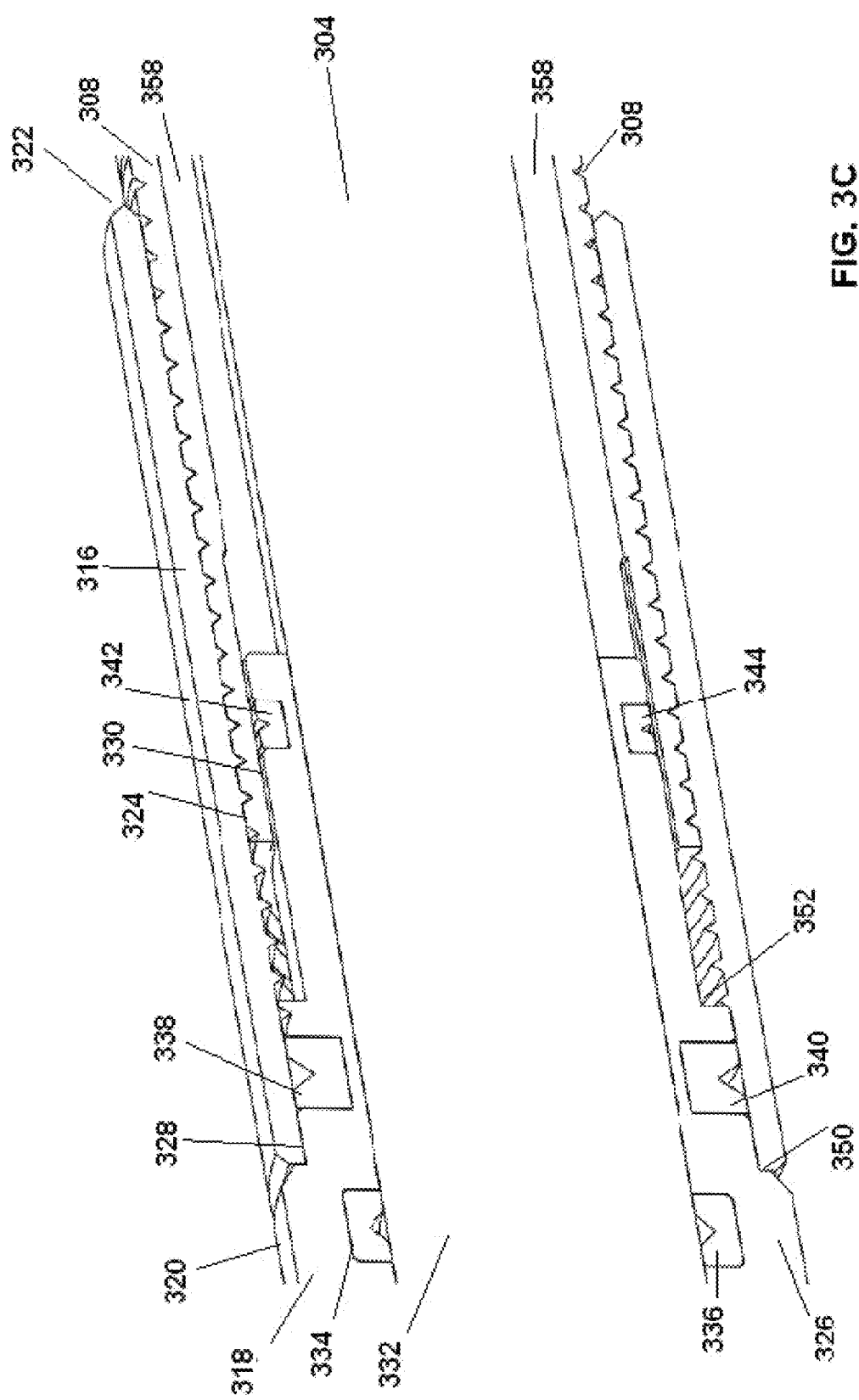

Early onset scoliosis (EOS) refers to the occurrence of a lateral spinal deviation in adolescents or children, for example, between four and nine years old. In these instances, a spinal fusion may not be appropriate because it can impede the growth process. Rather, an expandable rod, sometimes referred to as a "growing rod," may be implanted. These rods can be implanted along the curved segment of the spine and may be lengthened in situ, thereby growing along with the spinal column of the individual. Often, growing rods may be lengthened on a standard schedule, such as every three to six months, through a surgical procedure. These repeated surgical procedures can be invasive and accordingly can carry risks relating to wound healing and anesthesia, among other things. Additionally, the need for repeated surgical procedures can be time-consuming and costly. Accordingly, disclosed herein are new and improved spinal rods that can be extended in a minimally-invasive or non-invasive procedure.

Components of all of the devices disclosed herein can be made of materials known to those skilled in the art, including metals (e.g., titanium), metal alloys, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or copolymers thereof), allograft, and/or combinations thereof. In some embodiments, all components and/or all extendable rod assemblies described herein may be non-ferromagnetic (e.g., may not exhibit magnetic properties and/or may not be able to permanently produce a magnetic field). In these embodiments, individuals in whom the resulting assemblies are installed may advantageously be able to undergo medical imaging techniques such as MRI. The components can also be machined and/or manufactured using techniques known to those skilled in the art. For example, polymeric components may be injection-molded or blow-molded.

Figures 1A, 1B:
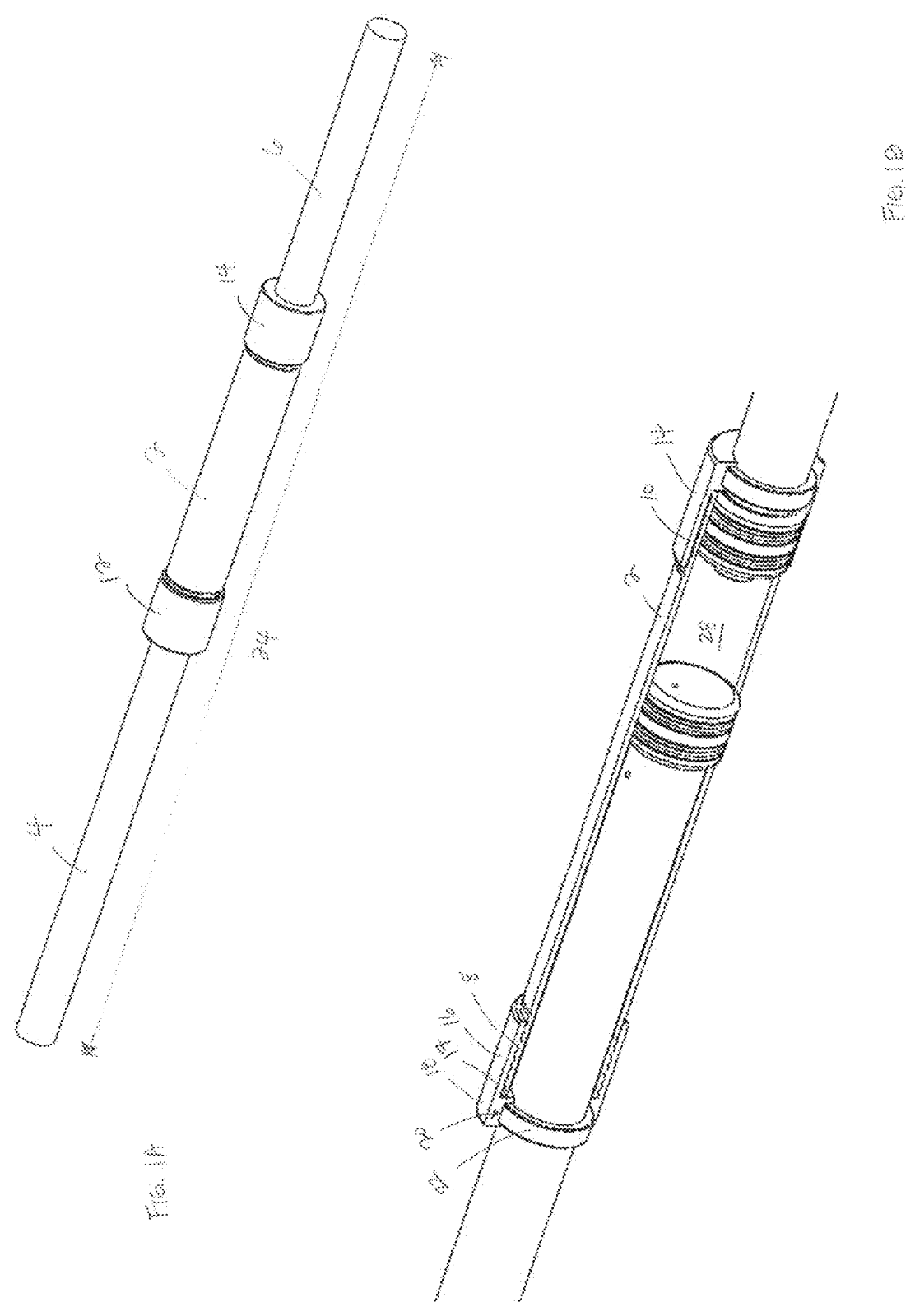

Turning now to FIGS. 1A-G, an extendable rod assembly 100 is illustrated in accordance with embodiments described herein. The extendable rod assembly 100 can include an elongate sleeve 2, an actuating rod 4, and a fixed rod 6. The extendable rod assembly 100 can also include a valve assembly 7, as illustrated in FIG. 1E, for example. The extendable rod assembly 100 may include a length 24 as measured from a distal-most end of the actuating rod 4 to a distal-most end of the fixed rod 6. Advantageously, the length 24 of the extendable rod assembly 100 may vary as the assembly 100 extends or retracts. In some embodiments, the length 24 of the assembly 100 may be configured to increase by about 5 cm to about 10 cm. In other embodiments, the length 24 of the assembly 100 may be able to increase by at least 7 cm. In yet other embodiments, the length 24 of the assembly 100 may be configured to increase by a factor in the range of from about 10% to about 50%. In other embodiments, the length 24 of the assembly 100 may be configured to increase by a factor in the range of from about 20% to abut 30%. In yet other embodiments, the length of the assembly 100 may be configured to increase by about 25%. As illustrated in FIG. 1A, the extendable rod assembly 100 can be configured to extend longitudinally in a straight line along its length 24. Those skilled in the art may appreciate that other embodiments of extendable rod assemblies described herein may also include one or more of these length characteristics.

As used herein, the terms "proximal" and "distal" are utilized generally with reference to the middle of the elongate sleeve of each extendable rod assembly. For example, the actuating rod 4 may have a proximal end and a distal end, wherein the proximal end is closer to the middle of the elongate sleeve than the distal end. For consistency, specific components may also follow this directional convention, regardless of their particular disposition with respect to the elongate sleeve 2. For example, a particular component of the actuating rod 4 that is disposed within the elongate sleeve 2 may be described with the same proximal-distal orientation as the actuating rod 4 as a whole, regardless of exactly where that particular component is disposed within the elongate sleeve 2.

As illustrated in FIG. 1A, the elongate sleeve 2 can be cylindrical (e.g., can include a circular transverse cross section, and a constant inner and/or outer diameter). In some embodiments, the elongate sleeve 2 can have an outer diameter in the range of from about 5 mm to about 10 mm. As illustrated in FIG. 1B, the elongate sleeve 2 can include a cannula 28 extending longitudinally therethrough. The cannula 28 can have a circular transverse cross-section and/or a constant diameter. The elongate sleeve 2 can include a first end 8 and a second end 10. In some embodiments, each of the first and second ends 8, 10 can include external threading. The first and second ends 8, 10 can be configured to engage or mate with first and second end caps 12, 14. For example, the first and second end caps 12, 14 can be configured to be disposed (e.g., threaded) onto the first and second ends 8, 10. The second end cap 14 can have some or all of the same features as the first end cap 12. The first end cap 12 can be cylindrical, e.g., can have a constant outer diameter. The first end cap 12 can also include a cannula passing longitudinally therethrough, which can also have a circular transverse cross-section. The first end cap 12 can include a proximal section 16 and a distal section 18. The proximal section 16 can include a first inner diameter and the distal section 18 can include a second inner diameter. As illustrated in FIG. 1B, the inner diameter of the proximal section 16 can be greater than the inner diameter of the distal section 18. The difference in inner diameters between the proximal section 16 and the distal section 18 may result in a ledge 17 at an interface where the two sections meet. The proximal section 16 can include interior threading. As described herein, the interior threading of the first end cap 12 can mate with the exterior threading of the elongate sleeve 2, thereby threading the first end cap 12 onto the elongate sleeve 2. The distal section 18 of the first end cap 12 can include an interior circumferential groove 20.

As illustrated in FIG. 1B, the interior circumferential groove 20 can be configured to receive a seal member 22 therein. The seal member 22, and any other seal members described herein, can be, for example, a square ring, an o-ring, or a gasket. In some embodiments, the seal member includes a square ring, and may be, for example, a wiper seal. In some embodiments, translating components (e.g., actuating rod) may include at least one square ring seal member and stationary components (e.g., fixed rod) may include at least one o-ring seal member. The seal member may also include additional features, such as a one-way valve. Various materials can be included in the seal member 22, and any other seal members described herein, such as thermoset polymers, thermoplastic polymers, elastomeric polymers, and synthetic rubbers. Some examples include, but are not limited to, ethylene propylene diene monomer (EPDM) rubber, fluoroelastomers (FKM), perfluoro-elastomers (FFKM), and tetrafluoro ethylene/propylene rubber (FEPM).

Turning to FIG. 1C, the actuating rod 4 can include an enlarged head 26 and a body 30 extending from the enlarged head 26. The body 30 can extend in a first distal direction. The body 30 can include a cylinder having a constant outer diameter. In these embodiments, the body 30 may have a circular transverse cross-section; in other embodiments, the body may have a different cross-sectional shape, such as triangular, square, rectangular, pentagonal, or hexagonal. In some embodiments, the body 30 can be solid. In other embodiments, the body 30 can be hollow (e.g., can include a cannula or other passageway extending at least partially therethrough). The diameter of the body 30 can vary, and may be, for example, in the range of from about 3 mm to about 10 mm. In some embodiments, the diameter of the body 30 can be in the range of from about 4 mm to about 7 mm. As illustrated in FIG. 1C, the enlarged head 26 can be configured to be disposed within the cannula 28 of the elongate sleeve 2. The outer diameter of the enlarged head 26 can be the same as or slightly smaller than the inner diameter of the elongate sleeve 2. For example, the enlarged head 26 and the elongate sleeve 2 may be engaged in a friction, interference, or slip fit. Additionally, the enlarged head 26 can have an outer diameter that is larger than an outer diameter of the body 30, as illustrated in FIGS. 1C-D. Accordingly, the enlarged head 26 can be configured to divide the cannula 28 into a first chamber 32 and a second chamber 34, illustrated in FIG. 1D. The outer diameter of the enlarged head 26 can also be greater than the inner diameter of the distal section 18 of the first end cap 12. Thus, when the enlarged head 26 is disposed within the elongate sleeve 2 and the first end cap 12 is threaded onto the first end 8, the enlarged head 26 may be trapped within the cannula 28. The enlarged head 26 can also include at least one exterior circumferential groove 36. As illustrated in FIG. 1D, the enlarged head 26 can include two exterior circumferential grooves. The exterior circumferential groove(s) 36 can be configured to receive a seal member 38 therein. In some embodiments, the seal member 38 is a square ring.

Those skilled in the art may appreciate that the actuating rod 4 may be configured to slide and/or translate longitudinally within the elongate sleeve 2. For example, the enlarged head 26 can travel between the first end cap 12 and the stem 50 of the fixed rod 6. Accordingly, the extendable rod assembly 100 can be configured to transition between a first configuration, wherein the assembly 100 is retracted, collapsed, shortened, un-expanded, and/or un-extended, and a second configuration, wherein the assembly 100 is lengthened, expanded, and/or extended. In the first configuration, the proximal surface 60 of the enlarged head 26 can contact a proximal surface 72 of the stem 50. In this configuration, the first chamber 32 may be relatively large and the second chamber 34 may be relatively small, as compared to the second configuration. In the second configuration, the distal surface of the enlarged head 26 can contact the ledge 17 of the first end cap 12. In this configuration, the first chamber 32 may be relatively small and the second chamber 34 may be relatively small, as compared to the first configuration. Those skilled in the art may appreciate that the assembly 100 may also be capable of numerous intermediate configurations, wherein the overall length of the assembly 100 is greater than the fully retracted length and less than the fully extended length.

As illustrated in FIG. 1C, the fixed rod 6 can include an enlarged head 40 and a body 42 extending from the enlarged head 40. The body 42 can extend in a second distal direction that is opposite of the body 30 of the actuating rod 4. The body 42 can include a cylinder having a constant outer diameter. In some embodiments, the body 42 can be solid. In other embodiments, the body 42 can be hollow (e.g., can include a cannula or other passageway extending at least partially therethrough). The diameter of the body 42 can vary, and may be, for example, in the range of from about 3 mm to about 10 mm. In some embodiments, the diameter of the body 42 can be in the range of from about 5 mm to about 7 mm. In other embodiments, the diameter of the body 42 of the fixed rod 6 can be the same as the diameter 30 of the actuating rod 4. As illustrated in FIG. 1C, the enlarged head 40 can be configured to be disposed within the cannula 28 of the elongate sleeve 2. The outer diameter of the enlarged head 40 can be the same as or slightly smaller than the inner diameter of the elongate sleeve 2. For example, the enlarged head 40 and the elongate sleeve 2 may be engaged in a friction or slip fit. Additionally, the enlarged head 40 can have an outer diameter that is larger than an outer diameter of the body 42, as illustrated in FIGS. 1C-D. The outer diameter of the enlarged head 40 can also be greater than the inner diameter of a distal section 44 of the second end cap 14. Thus, when the enlarged head 40 is disposed within the elongate sleeve 2 and the second end cap 14 is threaded onto the second end 10, the enlarged head 40 may be trapped within the cannula 28. The enlarged head 40 can include at least one exterior circumferential groove 46. As illustrated in FIG. 1D, the enlarged head 40 can include two exterior circumferential grooves. The exterior circumferential groove(s) 46 can be configured to receive a seal member 48 therein. In some embodiments, the seal member 48 is a square ring. As illustrated in FIG. 1D, the fixed rod 6 may further include a stem 50. The stem 50 may extend proximally from the enlarged head 40. The shape of the stem 50 can vary. In some embodiments, it may be cylindrical (e.g., the stem 50 may have a circular transverse cross-sectional shape). In other embodiments, it may be rectangular or may take on some other polygonal shape. As illustrated in FIG. 1D, the transverse cross-sectional area of the stem 50 may be smaller than a transverse cross-sectional area of the enlarged head 40. In embodiments where the stem 50 is cylindrical, the stem 50 may have a smaller diameter than the diameter of the enlarged head 40. Advantageously, the stem 50 may be used to maintain a gap between the actuating rod 4 and the fixed rod 6, thereby preventing the formation of a seal between these two members.

The extendable rod assembly 100 may also include a valve assembly. The valve assembly can be configured to control, regulate, and/or permit flow of a fluid between the first and second chambers 32, 34. In some embodiments, the extendable rod assembly 100 may include a needle valve assembly. Advantageously, the valve assembly may include an automatic valve that regulates flow in response to changes in fluid pressure. In some embodiments, the valve assembly can include a hydraulic or pneumatic actuation mechanism. Various fluids may be used in these valve assemblies, and may be selected on the basis of various factors, including, but not limited to compressibility, viscosity, and thermal conductivity, as well as consideration of the expected load or weight exerted on the assembly 100. Non-limiting examples of suitable fluids include air and saline.

Turning to FIG. 1E, one embodiment of a valve assembly 7 is illustrated. The valve assembly 7 can include a conduit 52 and a cavity 56 on a proximal portion of the body of the actuating rod 4, and a valve body 54. The conduit 52 can include an opening 58 on a proximal surface 60 of the enlarged head 26 of the actuating rod 4. The conduit 52 can extend longitudinally through the enlarged head 26 and a portion of the body 30 so as to intersect with the cavity 56. The conduit 52 can be in fluid communication with the cavity 56 and the second chamber 34.

The cavity 56 can be located at a proximal end of the body 30 of the actuating rod 4. The cavity 56 can extend along a transverse axis of the actuating rod 4. The cavity 56 can extend from a first opening 62 to a second opening 64, wherein both openings are on the body 30 of the actuating rod 4. The cavity 56 can be in fluid communication with the first chamber 32. The cavity 56 can have a shape that is configured to conform to the shape of the valve body 54. As illustrated in FIG. 1E, the cavity 56 can include a tapered portion, a cylindrical portion, and a threaded portion. The tapered portion of the cavity 56 may have the same dimensions as the tapered portion of the tapered portion of the valve body 54, described further herein. In some embodiments, the conduit 52 can intersect the tapered portion of the cavity 56.

The valve body 54 can be disposed within the cavity 56. The valve body 54 can include a stem 66 and a base 68. The stem 66 can include a tapered tip. As illustrated in FIG. 1E, the stem 66 can include a frustoconical tip. The stem 66 may be configured to be received within the tapered portion of the cavity 56. As illustrated in FIG. 1E, for example, the stem 66 may block the passage of fluid between the first chamber 32 and the second chamber 34. In particular, the tip of the stem 66 may block the second opening 64 and the conduit 52. The base 68 can be compressible, e.g., the volume occupied by the base 68 may be reversibly decreased. In some embodiments, the base 68 can include an elastic material (e.g., an elastomer). In other embodiments, the base 68 can include a spring member. Example materials that can be used for the base 68 include, but are not limited to, synthetic polymers such as nylon and other polyamides, silicones, polyurethanes, polyesters, and polyalkylene oxides. The base 68 may have a cylindrical shape and be configured to be received within the cylindrical portion of the cavity 56. In other embodiments, the base 68 may have a different shape.

As illustrated in FIG. 1E, the valve assembly 7 can further include a fastener 70. The fastener 70 can be configured to be received within the cavity 56 (e.g., the threaded portion). In some embodiments, the fastener 70 may be a set screw. In these embodiments, the fastener 70 may be configured to be threaded into the threaded portion of the cavity 56. In other embodiments, the fastener 70 may not include external threading (e.g., the fastener 70 may include a cam lock). In these embodiments, the cavity 56 may not include internal threading, but may include another feature configured to engage the fastener 70 (e.g., a cam groove). Advantageously, the fastener 70 may be configured to secure the valve body 54 within the cavity 56.

Embodiments herein are also directed to methods of installing the extendable rod assembly 100. In use, the first and second chambers 32, 34 may be filled with a fluid. As described herein, the particular fluid may be selected on the basis of the anticipated load that the extendable rod assembly 100 will bear, among other factors. The extendable rod assembly 100 may be installed in a retracted, collapsed, shortened, or un-extended configuration, using techniques known to those skilled in the art. In this configuration, the proximal surface 60 of the enlarged head 26 of the actuating rod 4 may rest against or be adjacent to the proximal surface 72 of the stem 50.

In some embodiments, the extendable rod assembly 100 may be used in conjunction with one or more other devices, including but not limited to a bone screw, intervertebral cage, artificial disc, stabilizing plate, or other prosthetics, to treat a spinal irregularity. In embodiments where the extendable rod assembly 100 is used to treat scoliosis or EOS, it may be configured to be coupled to a posterior section of a spine. In some embodiments, two assemblies 100 may be installed, with one on each side of a spinal column. The extendable rod assembly 100 may be coupled, fastened, or secured to a posterior section of a bone (e.g., a vertebra or a rib) through one or more fasteners (e.g., screws and/or hooks). In these embodiments, the fastener(s) may be installed prior to the extendable rod assembly 100. For example, pedicle screws may be installed in pedicles of a first (e.g., superior) vertebra above the curvature and a second (e.g., inferior) vertebra below the curvature. Any pedicle screws known in the art and configured to receive a rod may be used, including but not limited to monoaxial and polyaxial pedicle screws. After the fasteners are installed, the extendable rod assembly 100 may be installed by coupling the actuating rod 4 and the stationary rod 6 with the fasteners. In some embodiments, the actuating rod 4 and/or the stationary rod 6 may be secured or anchored, e.g., unable to pivot, rotate, and/or translate, relative to the fasteners and the respective vertebrae. In some embodiments, the actuating rod 4 may be coupled with the superior vertebra and the stationary rod 6 may be coupled with the inferior vertebra. However, the extendable rod assembly 100 can advantageously be installed with either rod extending in the superior direction, and vice versa. Thus, in other embodiments, the actuating rod 4 may be coupled with an inferior vertebra and the stationary rod 6 may be coupled with a superior vertebra.

As described herein, growing rods may be used to treat early onset scoliosis in children who may still be growing. Thus, after installation, the rod may need to be extended or lengthened in order to accommodate the child's growth. Advantageously, the extendable rod assembly 100 may be configured to extend and/or lengthen automatically, in vivo, without surgical or clinical intervention. In use, as the spine grows, the first and second vertebrae may be pulled apart, resulting in the actuating rod 4 and the fixed rod 6 being pulled apart. The fixed rod 6 may already be seated in the second end cap 14, and may therefore be unable to translate within the elongate sleeve 2 in the direction of the applied force. In contrast, the actuating rod 4 may be pulled in the distal (e.g., outward) direction, resulting in increased pressure in the first chamber 32 and reduced pressure in the second chamber 34. The valve assembly 7 may be used to equalize the pressure in the first and second chambers 32, 34. As the pressure increases in the first chamber 32, a force may be exerted on the valve body 54, which may cause the base 68 to compress, as illustrated in FIGS. 1G-H. Consequently, the stem 66 may be pushed down within the cavity 56 so that it is no longer blocking the second opening 64 and/or the conduit 52. Fluid may then be allowed to flow between the first chamber 32 and the second chamber 34, via the cavity 56 and conduit 52. As fluid flows between the first and second chambers 32, 34, the pressure within the two chambers may be equalized. Advantageously, as the spine grows, the extendable rod assembly 100 can continue to extend automatically in this manner. In addition to avoiding complications due to repeated invasive procedures, the automatic adjustment of the extendable rod assembly 100 may eliminate or reduce the need for repeated doctor's visits. This feature may be particularly helpful in situations where patients live far away from their doctors and/or are unable to visit their doctor on a regular basis.

Turning now to FIGS. 2A-D, an extendable rod assembly 200, which may optionally be referred to as a curved rod assembly, is illustrated in accordance with embodiments described herein. The extendable rod assembly 200 can include an elongate sleeve 202, an actuating rod 204, and a fixed rod 206. As described further herein, the extendable rod assembly 200 may advantageously be configured to extend longitudinally in a curved line.

As illustrated in FIG. 2B, the actuating rod 204 can include a two-piece body. The two-piece body can include a first segment 210 and a second segment 212, wherein the first segment 210 extends distally from the second segment 212. The first segment 210 can be pivotably coupled to the second segment 212 by a joint (e.g., a ball and socket joint). The first segment 210 can include a proximal portion 214 and the second segment 212 can include a distal portion 218. As described further herein, the first segment 210 can include a socket and the second segment 212 can include a rounded protrusion. In other embodiments, the first segment 210 can include a rounded protrusion and the second segment 212 can include a socket. As illustrated in FIGS. 2C-D, the proximal portion 214 of the first segment 210 can include a socket 216. The proximal portion 214 of the first segment 210 can include a first arm 224 and a second arm 226 defining the socket 216 therebetween. The first and second arms 224, 226 can be separated by a transverse channel or void 228 that extends through the proximal portion from a first outer surface to a second outer surface, intersecting the socket 216. Accordingly, the transverse channel or void 228 may be in fluid communication with the socket 216.

The distal portion 218 of the second segment 212 can include a neck 220 and a rounded protrusion 222 extending from the neck 220. The socket 216 can be configured to receive the rounded protrusion 222 therein. In some embodiments, the socket 216 can include a rounded inner surface. The curvature of the rounded inner surface can match (e.g., equal) the curvature of the rounded protrusion 222. A proximal portion of the first segment 210 (e.g., a proximal portion of the first and second arms 224, 226) may further include a ringed protrusion or rim 230. The rim 230 can define a passageway having a width that is less than a diameter of the rounded protrusion 222. The rounded protrusion 222 may thus be secured, trapped, or contained within the socket 216. However, the rounded protrusion 222 may also be configured to pivot or rotate within the socket 216.

The elongate sleeve 202 may take the shape of a curved tube and may extend longitudinally along a curved line. As illustrated in FIGS. 2A-B, the first segment 210 of the actuating rod 204 may also be curved, e.g., may extend longitudinally along a curved line. The first segment 210 may follow the same curvature as the elongate sleeve 202. In some embodiments, the actuating rod 204 and the elongate sleeve 202 may be concentric. The fixed rod 206 may also have a body portion 208 that can extend longitudinally along a straight or curved line. In some embodiments, the elongate sleeve 202, first segment 210 of the actuating rod 204, and/or the body portion 208 of the fixed rod 206 may be malleable (e.g., contourable, flexible, and/or bendable) and/or the curvature of these elements may be adjustable. Except as otherwise described, the extendable rod assembly 200 and its components may additionally include some or all of the same features (e.g., valve assembly 7) as specified with respect to the extendable rod assembly 100.

In use, the extendable rod assembly 200 may be installed, e.g., along a spine, as described herein with respect to extendable rod assembly 100. The actuating rod 204 may be pulled distally (e.g., outward) to extend or lengthen the assembly 200. As the actuating rod 204 travels along a curved path (e.g., as dictated by the curvature of the elongate cannula 202), the first and second segments 210, 212 may pivot with respect to one another, transferring force along the actuating rod 204 and/or enabling the actuating rod 204 to slide or translate smoothly. Advantageously, the jointed actuating rod 204 may enable or facilitate the use of curved assemblies, which may more closely match the contour or curvature of an individual's spine.

Turning now to FIGS. 3A-G, an alternative embodiment featuring an extendable rod assembly 300 is illustrated. The extendable rod assembly 300 can include an elongate sleeve 302, an actuating rod 304, and a fixed rod 306. The extendable rod assembly 300 can also include a valve assembly 307, as illustrated in FIG. 3E. The elongate sleeve 302 can include a first end 308, a second end 310, and a cannula 358 extending therethrough. In some embodiments, each of the first and second ends 308, 310 can include external threading. In some embodiments, the first and second ends 308, 310 may be symmetrical. In other embodiments, they may be asymmetrical. The first and second ends 308, 310 can be configured to engage or mate with first and second end caps 312, 314. For example, the first and second end caps 312, 314 can be configured to be disposed (e.g., threaded) onto the first and second ends 308, 310. The second end cap 314 can include some or all of the features as the first end cap 312. In other embodiments, the second end cap 314 can include some or all of the features as the first and/or second end caps 12, 14 as described herein with respect to the extendable rod assembly 100.

In some embodiments, the second end 310 of the elongate sleeve 302 may include a constricted section 380, as illustrated in FIG. 3G. The constricted section 380 can include an inner diameter that is smaller than adjacent of the elongate sleeve 302 on either side of the constricted section 380. As a result, the constricted section 380 may be bounded by a first ledge 382 and a second ledge 384. In some embodiments, the constricted section 380 is next to (e.g., proximal to) or located within the exteriorly-threaded section of the second end 310. The outer diameter of the constricted section 380 may be the same or different as other sections of the elongate sleeve 302. As described herein, the constricted section 380 may inhibit translational movement of the fixed rod 306 and/or may prevent contact between the actuating rod 304 and fixed rod 306, thereby preventing formation of a seal between these members.

Figure 3D:
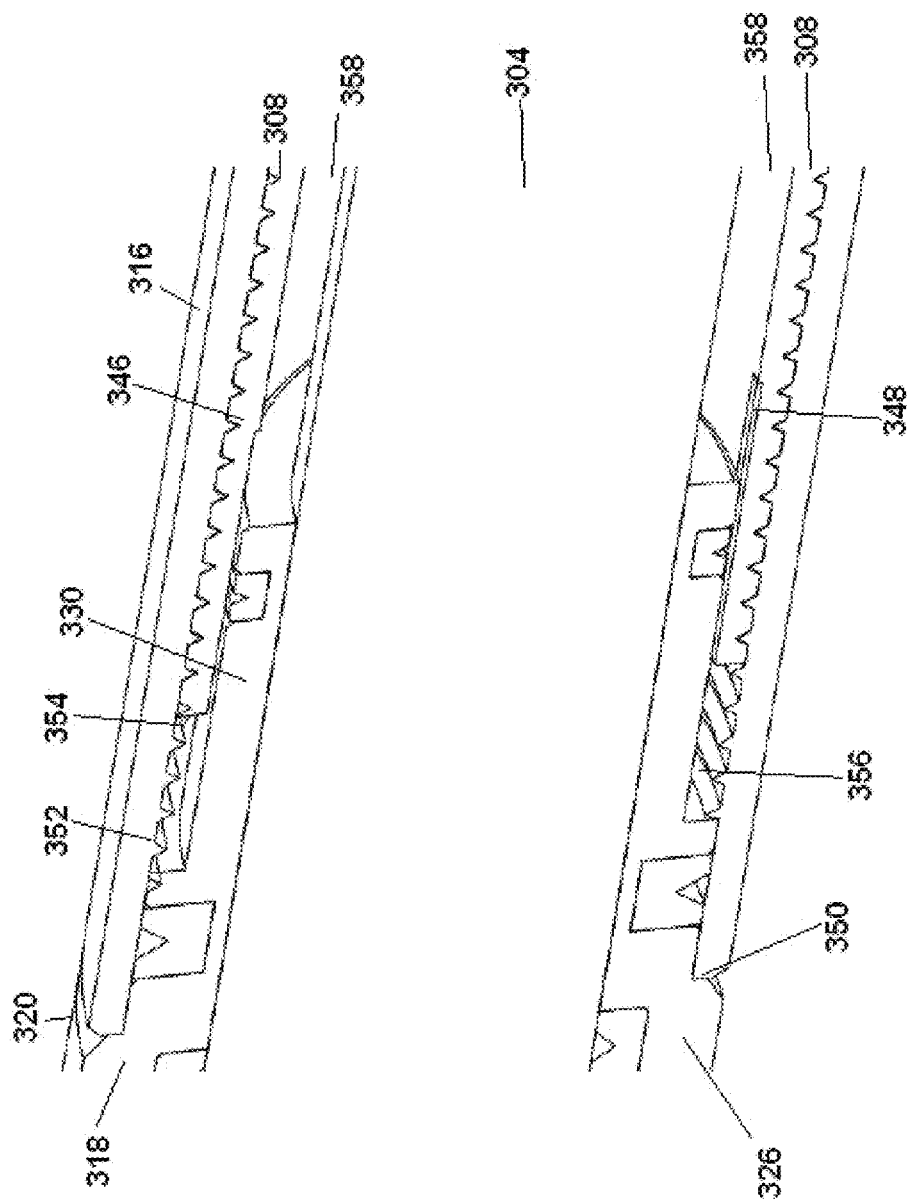

As illustrated in FIG. 3B, the first end cap 312 can include a hollow tube 316 and a rotatable stopper 318. As illustrated in FIG. 3C, the hollow tube 316 can include a first open end 320, a second open end 322, and an at least partially threaded inner surface 324. The hollow tube 316 can have an annular or ring-shaped transverse cross section. The first open end 320 can have an inner diameter that is equal to an inner diameter of the second open end 322. In some embodiments, the hollow tube 316 can have a constant inner and/or outer diameter. The threaded inner surface 324 may be configured to mate with the external threading on the first end 308 of the elongate sleeve 302. For example, the hollow tube 316 may be threaded onto the first end 308 of the elongate sleeve 302. As illustrated in FIG. 3C-D, the first open end 320 may be configured to contact or abut a portion of the rotatable stopper 318 (e.g., the enlarged head 326, described further herein).

As illustrated in FIG. 3C, the rotatable stopper 318 can include an enlarged head 326, an intermediate section 328, and a body 330. The enlarged head 326 may have a larger outer diameter than that of the intermediate section 328, and the intermediate section 328 may have a larger outer diameter than that of the body 330. Accordingly, the rotatable stopper 318 may include a ledge 350 at an interface between the enlarged head 326 and intermediate section 328, and a ledge 352 at an interface between the intermediate section 328 and the body 330. The rotatable stopper 318 can include a cannula 332 extending longitudinally therethrough. The intermediate section 328 and the body 330 can be configured to be received within the hollow tube 316. At least a portion of an outer surface of the body 330 may be configured to engage at least a portion of an inner surface of the first end 308 of the elongate sleeve 302. As illustrated in FIGS. 3B-C, the body 330 of the rotatable stopper 318 may be inserted into the first end 308 of the elongate sleeve 302. In some embodiments, the rotatable stopper 318 and the elongate sleeve 302 may be engaged in an interference, friction, or slip fit. For example, the rotatable stopper 318 may be configured to rotate, pivot, or twist within the elongate sleeve 302. The rotatable stopper 318 may further include one or more seal members. As illustrated in FIGS. 3B-C, the enlarged head 326 of the rotatable stopper 318 can include at least one interior circumferential groove 334 configured to receive a seal member 336. As illustrated in FIG. 3B, the enlarged head 326 can include two circumferential grooves 334 and two seal members 336 disposed therein. The intermediate portion 328 can include an exterior circumferential groove 338 configured to receive a seal member 340 therein. The body portion 330 can also include an exterior circumferential groove 342 configured to receive a seal member 344 therein. Any of the seal members described herein, e.g., wiper seals, can be used as seal members 336, 340, and 344.

The body 330 of the rotatable stopper can include at least one longitudinal groove 346, as illustrated in FIG. 3D. In some embodiments, two, three, four, or more longitudinal grooves can be disposed circumferentially about the body 330. As illustrated in FIG. 3D, an internal surface of the first end 308 of the elongate sleeve 302 can also include at least one longitudinal groove 348. In some embodiments, two, three, four, or more longitudinal grooves can be disposed circumferentially about the interior of the first end 308. The longitudinal grooves on the interior surface of the elongate sleeve 302 can be configured to align with the longitudinal grooves on the exterior surface of the body 330.

When assembled, the hollow tube 316 may be threaded onto the first end 308 of the elongate sleeve 302. The hollow tube 316 may not completely overlap the first end 308 of the elongate sleeve 302; instead, these two elements may be longitudinally staggered. The first open end 320 of the hollow tube 316 may extend distally as compared to a first end face 354 of the elongate sleeve 302, as illustrated in FIG. 3D. The body 330 of the rotatable stopper 318 may be inserted into the first end 308 of the elongate sleeve 302. As described herein, the body 330 may be engaged with the elongate sleeve 302 in a slip fit and may be configured to rotate within the elongate sleeve 302. A portion of the enlarged head 326 (e.g., ledge 350) may abut the first open end 320 of the hollow tube 316. As illustrated in FIG. 3D, this configuration may result in the creation of a gap 356 between the first end face 354 of the elongate sleeve 302 and the ledge 352 of the enlarged head 326.

In use, when the elongate grooves 346, 348 on the rotatable stopper 318 and the elongate sleeve 302 are not in alignment, the cannula 358 may not be in fluid communication with the gap 356. However, when the rotatable stopper 318 is rotated, the elongate grooves 346, 348 may be aligned, thereby allowing fluid communication between the cannula 358 and the gap 356 and effectively lengthening the cannula 358. As described herein with respect to the valve assembly 7 of extendable rod assembly 100, a fluid may be added to the cannula (e.g., first and/or second chambers 32, 34) at a particular pressure based on, among other things, the anticipated load that will be borne by the extendable rod assembly 100 in situ. The first end cap 312 described in the present embodiment advantageously permits the pressure in the assembly to be adjusted by twisting or rotating the rotatable stopper 318. Accordingly, the pressure may be easily varied, either before, during, or after installation.

Turning to FIG. 3E-F, the valve assembly 307 can include a duct 364 and a cavity 360 on a proximal portion of the actuating rod 304, and a valve body 362. As described herein with respect to the actuating rod 4 of the extendable rod assembly 100, the actuating rod 304 may include an enlarged head 366, which can be disposed within the elongate sleeve 302. The outer diameter of the enlarged head 366 may be equal to or slightly smaller than the inner diameter of the elongate sleeve 302, such that these two components may be engaged in a friction, interference, or slip fit. As illustrated in FIG. 3F, the enlarged head 366 may be configured to divide the cannula 358 into a first chamber 368 and a second chamber 370. The duct 364 may be in fluid communication with the first chamber 368 and the cavity 360, and the cavity 360 may be in fluid communication with the second chamber 370. In some embodiments, the duct 364 can extend from an outer surface (e.g., a side wall) of the actuating rod 304 to the cavity 360. The cavity 360 can extend at least partially along a longitudinal axis of the actuating rod 304.

The valve body 362 may regulate fluid flow between the first and second chambers 368, 370. As illustrated in FIGS. 3E-F, the valve body 362 can include a first extension member 363 extending proximally from the fixed rod 306. In some embodiments, the first extension member 363 can extend from a proximal-most surface 378 of the fixed rod 306. The first extension member 363 can be slideably disposed within the cavity 360. The first extension member 363 can include a first longitudinal cannula 372 extending at least partially through the first extension member 363. The first extension member 363 can also include a plurality of transverse conduits 374 in fluid communication with the first longitudinal cannula 372. In some embodiments, the first extension member 363 may include a number of transverse conduits 374 in the range of from about ten to about fifty. In other embodiments, the first extension member 363 may include a number of transverse conduits 374 in the range of from about twenty to about thirty. The transverse conduits 374 may be spaced apart longitudinally in regular intervals. Each transverse conduit 374 can extend from an outer surface of the first extension member 363 to the first longitudinal cannula 372. The transverse conduit 374 can take on a plurality of different shapes. For example, it may be a pin hole (e.g., circular opening) or a slot (e.g., rectangular opening). In some embodiments, each transverse conduit 374 can include a semicircular slot (e.g, semicircular as viewed along a transverse plane of the first extension member 363). In other embodiments, each transverse conduit 374 can extend along at least 25% of an outer circumference of the first extension member 363. In some embodiments, the first extension member 363 can include a plurality of transverse channels or grooves 376, as illustrated, for example, in FIG. 3E. The grooves 376 can extend circumferentially around the first extension member 363. Each transverse conduit 374 may be situated within a groove 376. Except as otherwise described, the extendable rod assembly 300 and its components may additionally include some or all of the same features as specified with respect to the extendable rod assembly 100 and/or 200. Additionally, those skilled in the art may appreciate that the valve assembly 307 and/or the first end cap 312, among other things, may be incorporated into the extendable rod assembly 100 and/or 200.

In use, the extendable rod assembly 300 may be installed, e.g., posteriorly along a spine, in a retracted, collapsed, or un-extended configuration as described herein with respect to the extendable rod assembly 100, for example. As the spine grows or lengthens, the distance between the first and second vertebrae to which the extendable rod assembly 300 is coupled or secured may increase, resulting in the actuating rod 304 and the fixed rod 306 being pulled apart. The fixed rod 306 may be seated in the second end cap 314, as illustrated in FIG. 3G. The constricted section 380 may inhibit the fixed rod 306 from translating within the elongate sleeve 302. In contrast, the actuating rod 304 may be pulled in the distal (e.g., outward) direction, resulting in increased pressure in the first chamber 368 and reduced pressure in the second chamber 370. The valve assembly 307 may be configured to equalize the pressure in the first and second chambers 368, 370. As the actuating rod 304 is pulled distally (e.g., outward), the pressure in the first chamber 368 may increase until the duct 364 enters fluid communication with a transverse conduit 374, as illustrated in FIG. 3G. As that point, fluid from the first chamber 368 is allowed to flow to the second chamber 370 through the transverse conduit 374 and the first longitudinal cannula 372. The groove 376 may promote channeling the fluid into the transverse conduit 374. The pressure in the first and second chambers 368, 370 may then be equalized. As the spine continues to grow, the pressure differential between the first and second chambers 368, 370 may increase until the next transverse conduit 374 reaches the duct 364. Advantageously, as the spine grows or lengthens, the extendable rod assembly 300 can continue to extend automatically in this manner.

Some embodiments can include two actuating rods and a valve assembly having two extension members. Turning now to FIGS. 4A-C, an alternative embodiment featuring an extendable rod assembly 400 is illustrated. The extendable rod assembly 400 can include an elongate sleeve 402, a first actuating rod 404, and a second actuating rod 406. The two actuating rods 404, 406 may both be configured to translate within the elongate sleeve 402 to increase the overall length of the extendable rod assembly 400. The extendable rod assembly 400 can also include a valve assembly 407, as illustrated in FIGS. 4B-C. The elongate sleeve 402 can include a first end 408, a second end 410, and a cannula 411 extending therethrough. The elongate sleeve 402 can be cylindrical (e.g., can include a circular transverse cross section and a constant inner and/or outer diameter). In some embodiments, the elongate sleeve 402 may have an outer diameter in the range of from about 5 mm to about 10 mm. The cannula 411 can have a circular transverse cross-section and/or a constant diameter. In some embodiments, the first and second ends 408, 410 can include external threading as illustrated in FIG. 4A, for example. In some embodiments, the first and second ends 408, 410 may be symmetrical. In other embodiments, they may be asymmetrical. The first and second ends 408, 410 can be configured to engage or mate with first and second end caps 412, 414. The first and second ends 408, 410 can be configured to engage or mate with first and second end caps 412, 414. For example, the first and second end caps 412, 414 can be configured to be disposed (e.g., threaded) onto the first and second ends 408, 410. The second end cap 414 can include some or all of the features as the first end cap 412. As illustrated in FIGS. 4A-C, the first and second end caps 412, 414 can include the same features as described herein with respect to the first end cap 312 of extendable rod assembly 300. For example, the first end cap 412 can include a hollow tube 416 and a rotatable stopper 418. The second end cap 414 may also include a hollow tube 417 and a rotatable stopper 419. In other embodiments, the first and/or second end cap 412, 414 can include some or all of the features as the first and/or second end caps 12, 14 as described herein with respect to the extendable rod assembly 100.

As illustrated in FIGS. 4B-C, the valve assembly 407 may include a valve body 420 configured to be disposed or situated within the cannula 411. The valve body 420 may include an enlarged head 422, a first extension member 428 extending from the enlarged head 422 in a first direction, and a second extension member 430 extending from the enlarged head 422 in a second direction opposite of the first extension member 428. The outer diameter of the enlarged head 422 can be the same as or slightly smaller than the inner diameter of the elongate sleeve 402. For example, the enlarged head 422 and the elongate sleeve 402 may be engaged in a friction or slip fit. Accordingly, the enlarged head 422 of the valve body 420 may be configured to divide the cannula 411 into a first chamber 424 and a second chamber 426. The first and second chambers 424, 426 may not be in fluid communication with each other. In some embodiments, the valve body 420 may further include a first stem disposed between the first extension member 428 and the enlarged head 422 and a second stem disposed between the second extension member 430 and the enlarged head 422. The first and second stems may each have a smaller diameter than that of the enlarged head 422 and/or may be configured to prevent the first and second actuating rods 404, 406 from contacting the enlarged head 422 and forming a seal. The enlarged head 422 can include at least one exterior circumferential groove 436. The exterior circumferential groove(s) may be configured to receive a seal member 438 therein. In some embodiments, the seal member 438 is an o-ring. In other embodiments, the seal member 438 may have one or more properties as described herein with respect to seal member 22 of extendable rod assembly 100. In some embodiments, the enlarged head 422 can include two exterior circumferential grooves and two o-rings seated therein, as illustrated in FIGS. 4B-C.

The first and/or second extension members 428, 430 may have some or all of the same features described herein with respect to the first extension member 363 of the extendable rod assembly 300. For example, the first extension member 428 can include a first longitudinal cannula extending at least partially therethrough. The first extension member 428 can also include a plurality of transverse conduits 432 in fluid communication with the first longitudinal cannula. In some embodiments, the first extension member 428 may include a number of transverse conduits 432 in the range of from about ten to about fifty. In other embodiments, the first extension member 428 may include a number of transverse conduits 432 in the range of from about twenty to about thirty. The transverse conduits 432 may be spaced apart longitudinally in regular intervals. Each transverse conduit 432 may extend from an opening on an outer surface of the first extension member 428 to the first longitudinal cannula. The transverse conduit 432 can take on a plurality of different shapes. For example, it may be a pin hole (e.g., circular opening) or a slot (e.g., rectangular opening). In some embodiments, each transverse conduit 432 can include a semicircular slot (e.g., semicircular as viewed along a transverse plane of the first extension member 428). In other embodiments, each transverse conduit 432 can extend along at least 25% of an outer circumference of the first extension member 428. In some embodiments, the first extension member 428 can include a plurality of transverse channels or grooves 434, as illustrated in FIG. 4C. The grooves 434 can extend circumferentially around the first extension member 428. Each transverse conduit 432 may be situated within a groove 434. The second extension member 430 may be identical (e.g., symmetrical) to the first extension member 428. For example, the second extension member 430 can include a second longitudinal cannula and a plurality of transverse conduits in fluid communication with the second longitudinal cannula.

The first actuating rod 404 may include some or all of the same features as the first actuating rod 304 in the extendable rod assembly 300. In some embodiments, the first actuating rod 404 may be identical to the first actuating rod 304. The first actuating rod 404 may include, for example, an enlarged head 440 and a body 442 extending from the enlarged head 440. The enlarged head 440 can be configured to be disposed, situated, or received within a portion of the cannula 411 of the elongate sleeve 402 (e.g., within the first chamber 424). The outer diameter of the enlarged head 440 can be the same as or slightly smaller than the inner diameter of the elongate sleeve 402. For example, the enlarged head 440 and the elongate sleeve 402 may be engaged in an interference, friction, or slip fit. Additionally, the enlarged head 440 can have an outer diameter that is larger than an outer diameter of the body 442, as illustrated in FIGS. 4B-C. Accordingly, the enlarged head 440 can be configured to divide the first chamber 424 into a first sub-chamber 444 and a second sub-chamber 446, illustrated in FIG. 4C. The outer diameter of the enlarged head 440 can also be greater than the inner diameter of the distal section of the rotatable stopper 418. Thus, when the enlarged head 440 is disposed within the first chamber 424 and the first end cap 412 is engaged with the first end 408, the enlarged head 440 may be trapped within the first chamber 424. The enlarged head 440 can also include at least one exterior circumferential groove 448. As illustrated in FIGS. 4B-C, the enlarged head 440 can include two exterior circumferential grooves. The exterior circumferential groove(s) 448 can be configured to receive a seal member 450 therein. In some embodiments, the seal member 450 is a square ring.

A proximal portion of the first actuating rod 404 may also include a duct (not shown, but analogous to duct 364 of extendable rod assembly 300) and a cavity 452. The duct may be in fluid communication with the first sub-chamber 444 and the cavity 452, and the cavity 452 may be in fluid communication with the second sub-chamber 446. In some embodiments, the duct can extend from an outer surface (e.g., a side wall) of the first actuating rod 404 to the cavity 452. The cavity 452 can extend at least partially along a longitudinal axis of the first actuating rod 404, and may be configured to receive at least a portion of the first extension member 428 therein. As illustrated in FIG. 4C, the first extension member 428 of the valve body 420 may extend through the first chamber 424 and into the cavity 452. The first extension member 428 may be configured to slide or translate along or within the cavity 452.

The second actuating rod 406 may include some or all of the same features as the first actuating rod 404. In some embodiments, the second actuating rod 406 may be identical to the first actuating rod 404. The second actuating rod 406 may include, for example, an enlarged head 454 and a body 456 extending from the enlarged head 454. The enlarged head 454 can be configured to be disposed, situated, or received within a portion of the cannula 411 of the elongate sleeve 402 (e.g., within the second chamber 426). The outer diameter of the enlarged head 454 can be the same as or slightly smaller than the inner diameter of the elongate sleeve 402. For example, the enlarged head 454 and the elongate sleeve 402 may be engaged in an interference, friction, or slip fit. Additionally, the enlarged head 454 can have an outer diameter that is larger than an outer diameter of the body 456, as illustrated in FIGS. 4B-C. Accordingly, the enlarged head 454 can be configured to divide the second chamber 426 into a third sub-chamber 458 and a fourth sub-chamber 460, illustrated in FIG. 4C. The outer diameter of the enlarged head 454 can also be greater than the inner diameter of the distal section of the rotatable stopper 419. Thus, when the enlarged head 454 is disposed within the second chamber 426 and the second end cap 414 is engaged with the second end 410, the enlarged head 454 may be trapped within the second chamber 426. The enlarged head 454 can also include at least one exterior circumferential groove 462. As illustrated in FIGS. 4B-C, the enlarged head 454 can include two exterior circumferential grooves. The exterior circumferential groove(s) 462 can be configured to receive a seal member 464 therein. In some embodiments, the seal member 464 is a square ring.

A proximal portion of the second actuating rod 406 may also include a duct 466 and a cavity 468. The duct 466 may be in fluid communication with the third sub-chamber 458 and the cavity 468, and the cavity 468 may be in fluid communication with the fourth sub-chamber 460. In some embodiments, the duct 466 can extend from an outer surface (e.g., a side wall) of the second actuating rod 406 to the cavity 468. The cavity 468 can extend at least partially along a longitudinal axis of the second actuating rod 406, and may be configured to receive at least a portion of the second extension member 430 therein. As illustrated in FIG. 4C, the second extension member 430 of the valve body 420 may extend through the second chamber 426 and into the cavity 468. The second extension member 430 may be configured to slide or translate along or within the cavity 468.

The valve assembly 407 can include the valve body 420, duct and cavity 452 on the first actuating rod 404, and duct 466 and cavity 468 on the second actuating rod 406. The valve body 420 may regulate fluid flow between the first and second sub-chambers 444, 446, and between the third and fourth sub-chambers 458, 460. In use, the extendable rod assembly 400 may be installed, e.g., posteriorly along a spine, in a retracted, collapse, or un-extended configuration as described herein with respect to the extendable rod assembly 100 and/or 300, for example. As the spine grows or lengthens, the distance between the first and second vertebrae to which the extendable rod assembly 400 is coupled or secured may increase, resulting in the first actuating rod 404 and the second actuating rod 406 being pulled apart. In contrast to the extendable rod assemblies 100 and/or 300, both actuating rods 404, 406 may be configured to translate within or along the elongate sleeve 402 in the direction of the applied force. For example, where the first actuating rod 404 is coupled with a superior vertebra and the second actuating rod 406 is coupled with an inferior vertebra, the first actuating rod 404 may extend, translate, or slide in the superior direction and the second actuating rod 406 may extend, translate, or slide in the inferior direction.

As described herein with respect to the extendable rod assembly 300, when the first actuating rod 404 is pulled in a first distal or outward (e.g., superior) direction, pressure in the first sub-chamber 444 may increase and pressure in the second sub-chamber 446 may decrease. Similarly, when the second actuating rod 406 is pulled in a second distal or outward (e.g., inferior) direction, pressure in the third sub-chamber 458 may increase and pressure in the fourth sub-chamber 460 may decrease. The valve assembly 407 may be configured to equalize the pressure in the four sub-chambers. As the first actuating rod 404 is pulled in a first distal direction, the pressure in the first sub-chamber 444 may increase until the duct (not shown) enters fluid communication with a transverse conduit 432. At that point, fluid from the first sub-chamber 444 is allowed to flow through the duct, transverse conduit 432, cavity 452, and another transverse conduit 432 to the second sub-chamber 446, thereby equalizing the pressure in the first and second sub-chambers 444, 446. Similarly, as the second actuating rod 406 is pulled in a second distal direction, the pressure in the third sub-chamber 458 may increase until the duct 466 enters fluid communication with a transverse conduit 470. At that point, fluid from the third sub-chamber 458 is allowed to flow to the fourth sub-chamber 460 through the duct 466, cavity 468, and another transverse conduit 470 to the fourth sub-chamber 460, thereby equalizing the pressure in the third and fourth sub-chambers 458, 460. As the spine continues to grow, the pressure differential between the first and second sub-chambers 444, 446 (and/or between the third and fourth sub-chambers 458, 460) may increase until the next transverse conduit on either of the first or second extension members 428, 430 reaches the duct on the respective actuating rod. Advantageously, as the spine grows or lengthens, the extendable rod assembly 400 can continue to extend automatically in this manner. Those skilled in the art may appreciate that an equal and opposite pressure may be applied to the first and second actuating rods 404, 406. Accordingly, both first and second actuating rods 404, 406 may move apart (e.g., outwards) at the same rate. Consequently, the elongate sleeve 402 may remain in the center of the assembly 400 (as measured, for example, along the overall length of the assembly). This embodiment may be particularly advantageous when treating a curvature in the middle of a spine, e.g., in the thoracic spine. Other embodiments that include extension in only one direction may be advantageous when treating a curvature in an upper or lower portion of a spine, e.g., in the lumbar spine.

Figure 5A:
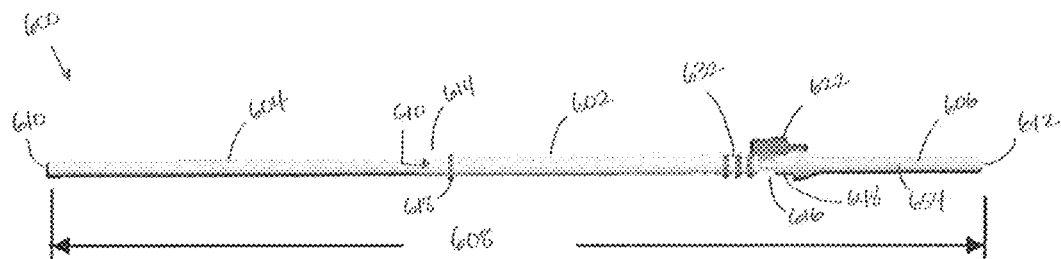
FIGS. 5A-C illustrate perspective views of an extendable rod assembly as described herein.
Figure 5B:
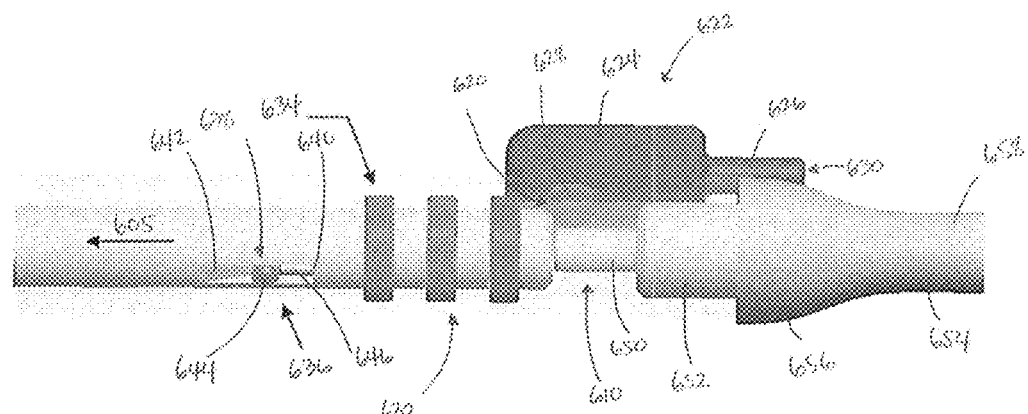
Figure 5C:
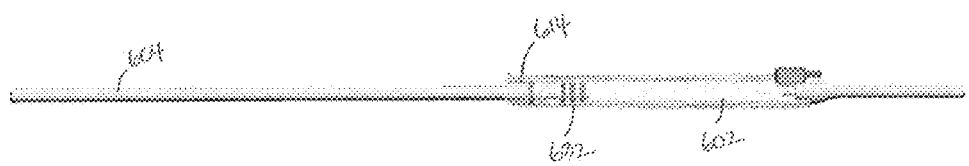

Turning now to FIGS. 5A-C, an alternative embodiment, extendable rod assembly 600, is illustrated. The extendable rod assembly 600 can include an elongate sleeve 602, an actuating rod 604, and a fixed rod 606. The extendable rod assembly 600 may include a length 608 that extends from a distal-most end 610 of the actuating rod 604 to a distal-most end 612 of the fixed rod 606. Advantageously, the length 608 of the extendable rod assembly 600 may vary as the assembly 600 extends or retracts. In some embodiments, the length 608 of the assembly 600 may be configured to increase by about 5 to about 10 cm. In other embodiments, the length 608 of the assembly 600 may be able to increase by at least 7 cm. In yet other embodiments, the length 608 of the assembly 600 may be configured to increase by a factor in the range of from about 10% to about 50%. In other embodiments, the length 608 of the assembly 600 may be configured to increase by a factor in the range of from about 20% to about 30%. In yet other embodiments, the length 608 of the assembly 600 may be configured to increase by about 25%. In some embodiments, the extendable rod assembly 600 can be configured to extend longitudinally in a straight line along its length 608. In other embodiments, the extendable rod assembly 600 may be configured to extend along a curved line.

As illustrated in FIGS. 5A-B, the elongate sleeve 602 may include a cannula 610 extending longitudinally therethrough. The elongate sleeve 602 can be cylindrical (e.g., can include a circular transverse cross section and a constant inner and/or outer diameter). In some embodiments, the elongate sleeve 602 may have an outer diameter in the range of from about 5 mm to about 10 mm. The cannula 610 may also have a circular transverse cross section and/or a constant diameter. As illustrated in FIGS. 5A-B, the elongate sleeve 602 may be straight (e.g., may remain longitudinally along a straight line). In other embodiments, the elongate sleeve 602 may be curved. The elongate sleeve 602 can include a first end 614 and a second end 616. In some embodiments, the first and/or second ends 614, 616 may be configured to receive first and/or second end caps thereon. The first and/or second ends 614, 616 may be configured to engage or mate with the first and second end caps, and may include, for example, external threading. In some embodiments, the second end 616 may not include external threading and/or an end cap.

As illustrated in FIG. 5A, the first end 614 may be configured to engage or receive a seal member 618 therein. For example, the first end 614 may include an internal circumferential groove, and the seal member 618 may be disposed within the groove. The seal member may have any of the properties as described herein with respect to seal member 22, and in some embodiments may be a wiper seal. The seal member 618 may be configured to prevent or reduce fluid leakage into or out of the cannula 610 via the first end 614. In some embodiments, the seal member 618 may include a one-way valve configured for degassing the cannula 610. The elongate sleeve 602 may additionally include a port 620, as illustrated in FIG. 5B. The port 620 may be configured to transfer a fluid in and out of the cannula 610. The port 620 may be located at the second end 616 of the elongate sleeve 602. In some embodiments, the port 620 includes a conduit or hole passing through a side wall of the elongate sleeve 602. The port 620 may connect the cannula 610 with an outer surface of the elongate sleeve 602. In some embodiments, the port 620 may be configured to couple directly with a fluid source.

In other embodiments, the assembly 600 may further include a fluid connector 622. The fluid connector 622 may be configured to direct a fluid into and/or out of the cannula 610 through the port 620. As illustrated in FIG. 5B, the fluid connector 622 can include a body 624, an inflow member 626, and an outflow member 628. It is noted that the terms "inflow member" and "outflow member" are non-limiting with regards to the direction of fluid flow within these members. As described further herein, fluid may flow both into and out of the inflow member and the outflow member, respectively. The inflow member 626 may include an inlet opening 630 and a lumen that extends from the inlet opening 630 to the body 624. In some embodiments, the inflow member 626 may be configured to be inserted into a tube or hose of a fluid source. For example, the inflow member 626 may include a hollow cylinder having a tapered exterior surface and at least one back-out prevention member disposed on the tapered exterior surface. In some embodiments, the back-out prevention member may be a slanted ring or a ridge. As another example, the inflow member 626 may include a hose barb. In some embodiments, the assembly 600 may additionally include a tube or hose that is coupled with the inflow member 626 and that is configured to receive a fluid, e.g., via pump or injection. The inflow member 626 may include a longitudinal axis that is orthogonal or perpendicular to a longitudinal axis of the outflow member 628. The outflow member 628 may include an outlet opening and a lumen that extends from the outlet opening to the body 624. The lumen may have a transverse cross-sectional area that is greater than a transverse cross-sectional area of the outlet opening. In some embodiments, the outlet opening may include a nozzle, such as a membrane nozzle. The body 624 may also include a conduit which may be in fluid communication with the lumen of the inflow member 626 and/or the lumen of the outflow member 628. Accordingly, the fluid connector 622 may include a passageway that extends from the inlet opening 630 to the outlet opening. In some embodiments, the fluid connector 622 may include a valve configured to regulate fluid flow through the passageway.

As illustrated in FIG. 5B, the outflow member 628 of the fluid connector 622 may be configured to engage with, e.g., be inserted into, the port 620 of the elongate sleeve 602. The outflow member 628 may be reversibly or irreversibly coupled with the port 620. For example, the outflow member 628 may be irreversibly coupled or connected to the port 620 by a method such as welding, soldering, or use of an adhesive. In some embodiments, the outflow member 628 may be configured engage the port 620 in a friction or interference fit. In other embodiments, the outflow member 628 may be configured to be threaded into the port 620. In these embodiments, the port 620 may also include internal threading. In yet other embodiments, the outflow member 628 and the port 620 may be configured to engage one another using a cam mechanism. The extendable rod assembly 600 may additionally include a coupling member configured to couple the outflow member 628 to the port 620 and/or to prevent or reduce leakage. Examples of suitable coupling members include, but are not limited to, a compression fitting, a seal member, and a fastener.

At least a portion of the actuating rod 604 can be disposed within the cannula 610 at the first end 614 of the elongate sleeve 602. Additionally, a portion of the actuating rod 604 may extend distally beyond (e.g., out of) the first end 614 of the elongate sleeve 602. As illustrated in FIG. 5A, for example, the distal-most end 610 of the assembly 600 may also be the distal-most end of the actuating rod 604. The actuating rod 604 may extend almost all the way through the cannula 610. As illustrated in FIGS. 5A-B, for example, when in the collapsed configuration, a proximal end 632 of the actuating rod may be near the second end 616. As illustrated in FIGS. 5A-C, the actuating rod 604 may be straight (e.g., may extend longitudinally along a straight line). In other embodiments, it may be a curved rod. As illustrated in FIGS. 5A-C, the actuating rod 604 may have a circular transverse cross-section. In other embodiments, the actuating rod 604 may have a different cross-sectional shape, such as triangular, square, rectangular, pentagonal, or hexagonal. In some embodiments, the actuating rod 604 can be solid. In other embodiments, the actuating rod 604 can be hollow (e.g., can include a cannula or other passageway extending at least partially therethrough). In some embodiments, the actuating rod can include an elongate cylinder having a constant outer diameter. The diameter of the actuating rod 604 can vary, and may be, for example, in the range of from about 3 mm to about 10 mm. In some embodiments, the diameter of the actuating rod 604 can be in the range of from about 4 mm to about 7 mm. The outer diameter of the actuating rod 604 may be less than the inner diameter of the elongate sleeve 602 (e.g., less than the diameter of the cannula 610). In some embodiments, the outer diameter of the actuating rod 604 may be equal to or slightly less than the inner diameter of the portion of the elongate sleeve 602 that includes the seal member 618. Accordingly, the actuating rod 604 may be engaged with the seal member 618 in a slip fit.

As illustrated in FIG. 5B, the proximal end 632 of the actuating rod 604 may be configured to engage or receive at least one seal member 634 thereon. For example, the proximal end 632 may include an external circumferential groove, and the seal member 634 may be disposed within the groove. The seal member 634 may have any of the properties as described herein with respect to seal member 22, and in some embodiments may be square ring or an o-ring. In some embodiments, the proximal end 632 may be configured to receive a plurality of seal members (e.g., two, three, four, five, or more). For example, as illustrated in FIG. 5B, the proximal end 632 may be configured to receive three seal members thereon. In these embodiments, each seal member may be staggered longitudinally along the actuating rod 604. The outer diameter of a portion of the actuating rod 604 having a seal member 634 disposed thereon (e.g., the combined diameter of the actuating rod 604 and the seal member 634) may be greater than a portion of the actuating rod 604 that does not include a seal member, as illustrated in FIG. 5B. This outer diameter may also be greater than the inner diameter of the portion of the elongate sleeve 602 having seal member 618 disposed therein. Advantageously, the seal member 618 may thereby act as a stopper to prevent the proximal end 632 of the actuating rod 604 from exiting the first end 614 of the elongate sleeve 602.

Those skilled in the art may appreciate that the actuating rod 604 may be configured to slide and/or translate longitudinally within the elongate sleeve 602. Accordingly, the extendable rod assembly 600 can be configured to transition from a first configuration, wherein the assembly 600 is retracted, collapsed, shortened, un-expanded, and/or un-extended, as illustrated in FIGS. 5A-B, and a second configuration, wherein the assembly 600 is lengthened, expanded, and/or extended, as illustrated in FIG. 5C. In the first configuration, the proximal end 632 of the actuating rod 604 can contact or be adjacent to the fixed rod 606 and the length 608 of the assembly 600 may be minimized. In the second configuration, the proximal end 632 of the actuating rod 604 may reach the first end 614 of the elongate sleeve 602 and the length 608 of the assembly 600 may be maximized. Those skilled in the art may appreciate that the assembly 600 may also be capable of numerous intermediate configurations, wherein the overall length of the assembly 600 is greater than the fully retracted length and less than the fully extended length.

As illustrated in FIG. 5B, the actuating rod 604 can also include at least one locking member 636. In some embodiments, the locking member 636 may be disposed anywhere along the actuating rod 604 (e.g., a proximal, intermediate, or distal portion). As illustrated in FIG. 5B, the locking member 636 can be disposed on the proximal end 632 of the actuating rod 604. The proximal end 632 can include a tapered groove 638, and the locking member 636 may be disposed within the tapered groove 638. The tapered groove 638 may extend longitudinally along an external surface of the actuating rod 604. As illustrated in FIG. 5B, the tapered groove 638 may have a first depth at a proximal end 640 and a second depth at a distal end 642, wherein the first depth is greater than the second depth. As described further herein, the locking member 636 may be configured to inhibit the actuating rod 604 from moving or sliding into the cannula 610 (e.g., may prevent or inhibit collapsing or shortening of the assembly 600). For example, the locking member 636 can include a spherical member 644 which may be coupled to a spring member 646. In some embodiments, the locking member 636 may be a spring-loaded ball. In some embodiments, the actuating rod 604 can include a plurality of locking members 636, e.g., two, three, four, or more. In these embodiments, the locking members 636 may be distributed around the circumference of the proximal end 632. In other embodiments, the locking members 636 may be arranged in series longitudinally on the actuating rod 604.

As illustrated in FIG. 5A, the fixed rod 606 may include a head 648 and a body 654. At least a portion of the fixed rod 606, e.g., head 648, may be disposed within the cannula 610 at the second end 612 of the elongate sleeve 602. As illustrated in FIG. 5B, the head 648 may include a stem 650 and an intermediate portion 652. The intermediate portion 652 may connect the head 648 to the body 654. The stem 650 may be generally cylindrical and may have an outer diameter that is less than the diameter of the cannula 610. Advantageously, the stem 650 may be used to maintain a gap between the actuating rod 604 and the fixed rod 606, thereby preventing the formation of a seal between these two members. The intermediate portion 652 may be configured to engage an inner surface of the elongate sleeve 602. In some embodiments, the intermediate portion 652 may also be generally cylindrical and may have an outer diameter that is slightly less than or equal to the diameter of the cannula 610. For example, the intermediate portion 652 may be configured to engage the inner surface of the elongate sleeve 602 in a friction or interference fit. In some embodiments, the intermediate portion 652 may be permanently attached or affixed within the cannula 610 (e.g., via welding, soldering, or adhering). The body 654 may extend towards the distal-most end 612, in a direction opposite of the actuating rod 604. As illustrated in FIG. 5B, the body 654 may include a proximal tapered portion 656 and a distal elongate portion 658. The tapered portion 656 may have a transverse cross-sectional area that decreases in the distal direction (e.g., towards the distal-most end 612), and the elongate portion 658 may have a constant transverse cross-sectional area. As illustrated in FIGS. 5A and C, the elongate portion 658 may be straight (e.g., may extend longitudinally along a straight line). In other embodiments, it may be curved. The elongate portion 658 may have a circular transverse cross-section. In other embodiments, the elongate portion 658 may have a different cross-sectional shape, such as triangular, square, rectangular, pentagonal, or hexagonal. In some embodiments, the fixed rod 606 may be solid. In other embodiments, the fixed rod 606 may be hollow (e.g., can include a cannula or other passageway extending at least partially therethrough). In some embodiments, the elongate portion 658 can include an elongate cylinder having a constant outer diameter. The diameter of the cylindrical portion 658 can vary, and may be, for example, in the range of from about 3 mm to about 10 mm. In some embodiments, the diameter of the cylindrical portion 658 can be in the range of from about 5 mm to about 7 mm. In other embodiments, the outer diameter of the cylindrical portion 658 of the fixed rod 606 can be the same as the outer diameter of the actuating rod 604.

Embodiments herein are also directed to methods of extending the extendable rod assembly 600. In use, the extendable rod assembly 600 may be provided in a retracted, collapsed, shortened, and/or un-extended configuration having a first length. In this configuration, the proximal end 632 of the actuating rod 604 may rest against or be adjacent to the stem 650 of the fixed rod 606. In embodiments where the extendable rod assembly 600 is being used to treat EOS, the extendable rod assembly 600 may be installed along a spine in the retracted configuration as described with respect to other extendable rod assemblies disclosed herein. In some embodiments, a tube or hose may be coupled with the fluid connector 622 either before or after installation of the assembly 600. The tube or hose coupled with the fluid connector 622 may advantageously be implanted subcutaneously.

The method of extending the extendable rod assembly 600 may then include coupling the port 620 with a fluid source. In some embodiments, the port 620 may be coupled directly to a fluid source. In other embodiments, the port 620 may be coupled indirectly to a fluid source through the fluid connector 622. For example, this step may include attaching or coupling a tube with the inflow member 626. In yet other embodiments, the port 620 may be coupled indirectly to a fluid source through the fluid connector 622 and the tube or hose coupled to the inflow member 626 of the fluid connector 622. For example, this step may include inserting a nozzle into the tube or hose.

The method may then include the step of introducing the fluid into the cannula 610. This step can include actuating the fluid source. Various fluids may be used to extend the extendable rod assembly 600 and may be selected on the basis of various factors, including, but not limited to compressibility, viscosity, and thermal conductivity, as well as consideration of the expected load or weight exerted on the assembly 600. Non-limiting examples of suitable fluids include air and saline. Additionally, various sources of fluid as known to those skilled in the art may be used. For example, in some embodiments, the fluid source can include a pump and/or injector. In other embodiments, it can include a saline injector. The fluid source may also be actuated using any appropriate methods, including manually and/or electronically.

In use, as the fluid enters the cannula 610, it may exert a pressure on the actuating rod 604, causing the actuating rod 604 to translate distally (e.g., outwards) in the direction indicated by arrow 605 and at least partially out of the cannula 610, thereby extending the extendable rod assembly 600 to a second length that is greater than the first length. Those skilled in the art may appreciate that the locking member 636 may not prevent motion of the actuating rod 604 in the distal direction. As the actuating rod 604 is pushed distally, the spring member 646 may compress and the spherical member 644 may rest in the deep proximal end 640 of the tapered groove 630.

After the assembly 600 has been extended, the fluid may optionally be removed from the cannula 610. This step may include, for example, using gravitational forces to allow the fluid to drain through a tube or hose that is coupled to the port 620, either directly or indirectly via the fluid connector 622. In other embodiments, this step may include applying a vacuum or other source of negative pressure to actively pump the fluid out. As the fluid is removed or drained, the locking member 636 may advantageously prevent the actuating rod 604 from retracting back into the cannula 610. For example, as the actuating rod 604 is pulled proximally, the spherical member 644 may roll towards the shallow distal end 642 of the tapered groove 638. While in the shallow part of the groove 638, the spherical member 644 may engage or contact the inner surface of the elongate sleeve 602 in an interference or friction fit, thereby inhibiting further movement of the actuating rod 604 in the proximal direction. As described herein, in embodiments that include a tube or hose coupled with the fluid connector 622, the tube or hose may be implanted subcutaneously. Thus, subsequent lengthening procedures (e.g., every three to six months) may be advantageously performed in a subcutaneous and/or minimally-invasive procedure. Such a procedure may require less time for surgery and recovery as compared to a more invasive extension procedure, and may also reduce risks to a patient.

Figure 6A:
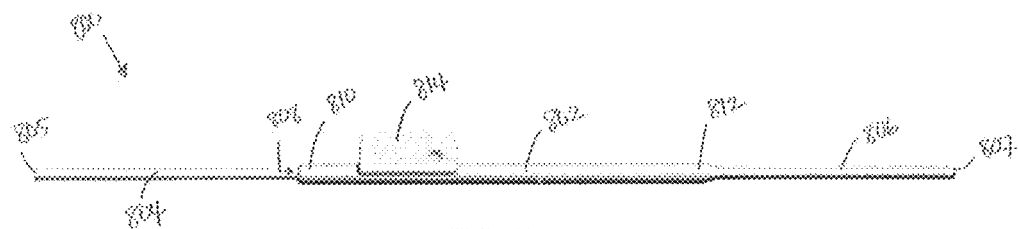
FIGS. 6A-F illustrate perspective views of an extendable rod assembly as described herein.
Figure 6B:
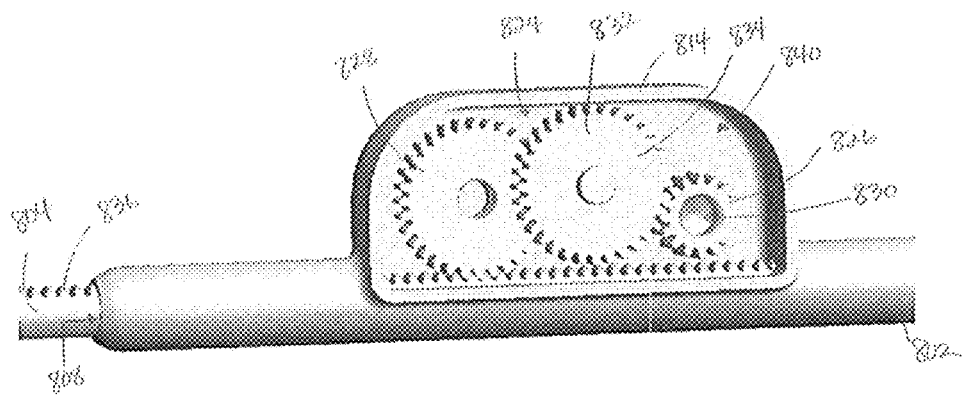

Turning now to FIGS. 6A-F, an alternative embodiment, extendable rod assembly 800, is illustrated. As illustrated in FIG. 6A, the extendable rod assembly 800 can include an elongate sleeve 802, an actuating rod 804, and a fixed rod 806. The elongate sleeve 802 can include a conduit 808 extending therethrough from a first end 810 to a second end 812. The elongate sleeve 802 can also include a housing member 814. As illustrated in FIG. 6B, the housing member 814 may be disposed on the elongate sleeve 802. In other embodiments, the housing member 814 may be integral with the elongate sleeve 802. In yet other embodiments, the housing member 814 may be reversibly coupled with the elongate sleeve 802. The housing member 814 may include a cavity 840 in fluid communication with the conduit 808. As illustrated in FIGS. 6A-B, for example, the elongate sleeve 802 may be generally cylindrical (e.g., may have a circular transverse cross-section, and may include a constant inner and/or outer diameter). In some embodiments, the elongate sleeve 802 may have an outer diameter in the range of from about 5 mm to about 10 mm. The elongate sleeve 802 may extend longitudinally along a straight or curved line (e.g., can accommodate a straight or curved rod).

As described further with respect to an alternative embodiment, elongate sleeve 803, the elongate sleeve 802 may include at least one guide member disposed within the conduit 808, e.g., at the first end 810. The guide member may include a channel configured to receive the actuating rod 804 therethrough. Advantageously, the guide member may be configured to stabilize the actuating rod 804 as it translates through the elongate sleeve 802, as described further herein. The elongate sleeve 802 may also include a retaining member disposed within the conduit 808, e.g., at the second end 812, and that may be configured to secure the fixed rod 806 within the elongate sleeve 802. The elongate sleeve 802 may also be configured to couple with one or more seal members. For example, in some embodiments, the first end 810 and/or the second end 812 of the elongate sleeve 802 may include an internal circumferential groove configured to receive a seal member therein. In some embodiments, the internal circumferential groove may be disposed on the guide member. The seal member may be, for example, an o-ring, a square ring, or any other seal members as described herein.

Figure 6C:
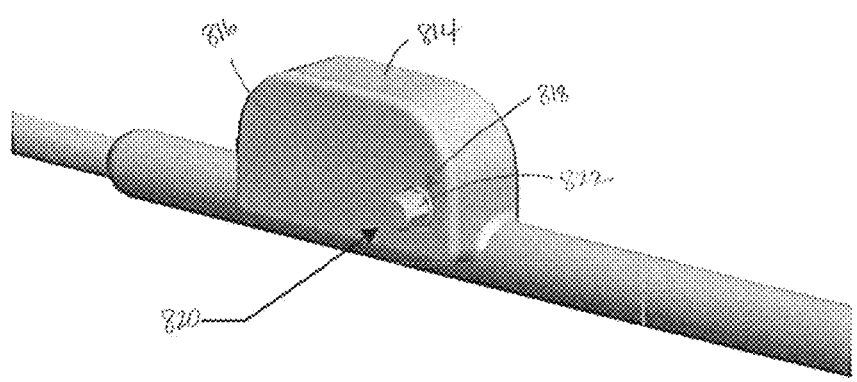
Figure 6D:
Figure 6E:
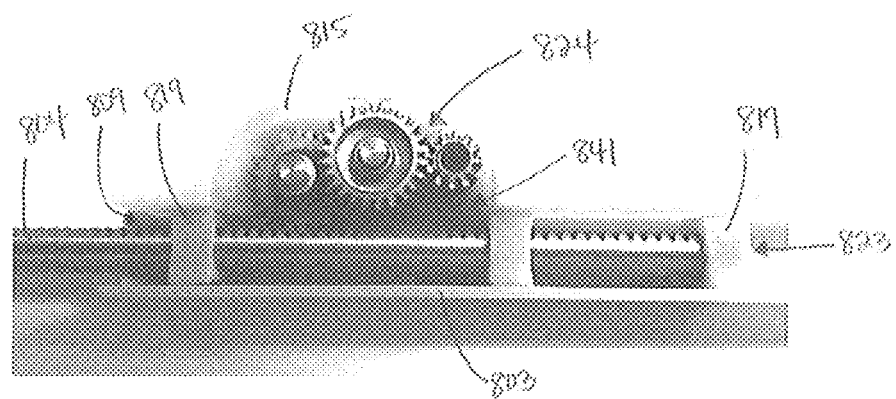
Figure 6F:
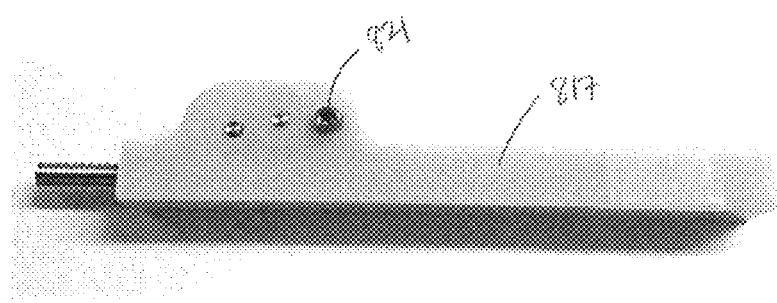

In some embodiments, the elongate sleeve 802 may include a cover. As illustrated in FIG. 6C, the housing member 814 may include a cover 816. An alternative embodiment, elongate sleeve 803 including cover 817, is illustrated in FIGS. 6E-F. The cover 816 may be configured to shield, protect, or enclose the housing member 814. The cover 816 may be configured to permanently or irreversibly mate with or engage the housing member 814, e.g., by welding, soldering, or adhering. In other embodiments, the cover 816 may be configured to temporarily or reversibly mate with or engage the housing member 814, e.g., by the use of fasteners or a snap fit between the two components. In some embodiments, the assembly 800 may include a seal member between the housing member 814 and the cover 816. The cover 816 may include an aperture 818. The aperture 818 may be configured to receive a drive member 820 therein. The drive member 820 may be rotatably disposed within the aperture 818. The drive member 820 may be configured to engage a gear assembly, described further herein, and/or a driver. In some embodiments, the drive member 820 may include a driver interface section 822 and a gear interface section. As illustrated in FIG. 6C, the driver interface section 822 may be configured to extend out of the housing member 814. The driver interface section 822 may include a protrusion, as illustrated in FIG. 6C, or a socket, as illustrated in FIG. 6F. The driver interface section 822 may include a transverse cross-sectional shape selected from the group consisting of circular, triangular, square, rectangular, pentagonal, and hexagonal. In some embodiments, the driver interface section 822 may include a hexagonal protrusion, as illustrated in FIG. 6C, or a hexagonal socket, as illustrated in FIG. 6F with regards to driver member 821. The aperture 818 may also be configured to receive a seal member. The seal member may advantageously prevent, reduce, or inhibit leakage into or out of the housing member 814 via the aperture 818.

An alternative embodiment of an elongate sleeve 803 is illustrated in FIGS. 6E-F. In this embodiment, the elongate sleeve 803 may include a housing member 815 that is integral with the elongate sleeve 803. Additionally, in these embodiments, the elongate sleeve 803 may not include an enclosed tube. Accordingly, the elongate sleeve 803 may also include a cover 817 that is configured to shield, protect, or enclose both the conduit 809 of the elongate sleeve 803 and the cavity 841 of the housing member 815. Except as otherwise described, the elongate sleeve 803 and its associated components (including, but not limited to, housing member 815, cover 817, and drive member 821) may include one or more of the same features as the elongate sleeve 802 and its associated components (including, but not limited to, housing member 814, cover 816, and drive member 820). For example, the elongate sleeve 803 may include one or more guide members 819. Each guide member 819 may include a channel 823 configured to receive the actuating rod 804 therethrough.

As illustrated in FIGS. 6B and 6E, the extendable rod assembly 800 may further include a gear assembly 824. The gear assembly 824 may be disposed or mounted in the housing member 814 or 815. The gear assembly 824 may be configured to actuate or translate the actuating rod 604, for example, using a rack and pinion mechanism. In some embodiments, the gear assembly 824 can include one gear. In other embodiments, the gear assembly 824 can include a series of gears, e.g., a gear train that can include two, three, four, or more gears. As illustrated in FIG. 6B, the gear train can include an input gear 826 and an output gear 828. The input gear 826 can be configured to engage the drive member 820 or 821. For example, the input gear 826 can include a socket 830 that is configured to receive the drive member 820 or 821. The output gear 828 may be configured to engage the actuating rod 804. For example, the output gear 828 may have teeth that are configured to mesh with teeth on the actuating rod 804. The output gear 828 may be referred to as a pinion.

In some embodiments, the gear assembly 824 can include four gears. In these embodiments, two of the four gears may be joined or affixed together as a compound gear 832. The compound gear 832 may include a first, larger gear 834 sharing an axle with and/or mounted on a second, smaller gear, wherein the larger gear 834 is configured to mesh with the input gear 826 and the smaller gear is configured to mesh with the output gear 828. The input gear 826 and the second, smaller gear may each have a number of teeth that is half of that of the larger gear 834 and the output gear 828. For example, the input gear 826 and the smaller gear may each include sixteen teeth, and the output gear 828 and the larger gear 834 may each include thirty-two teeth. In these embodiments, the gear train may have a gear ratio of 4:1.

In other embodiments, the gear assembly 824 can include three gears. In these embodiments, the gear train may include input gear 826, output gear 828, and an idler gear (not shown). The idler gear may be configured to mesh with both the input gear 826 and the output gear 828. The input gear 826 and the idler gear may each have a number of teeth that is half of that of the output gear 828. For example, the input gear 826 and the idler gear may each have sixteen teeth and the output gear 828 may include thirty-two teeth. In these embodiments, the gear train may have a gear ratio of 2:1.

When turned in a clockwise motion, the input gear 826 may cause the actuating rod 804 to translate distally out of the elongate sleeve 802. The gear assembly 824 may be configured such that one revolution of the drive member 820 or 821 can cause the actuating rod 804 to translate by a distance in the range of from about 4 mm to about 12 mm. In other embodiments, one revolution of the drive member 820 or 821 may cause the actuating rod 804 to translate by a distance in the range of from about 4 mm to about 6 mm. In yet other embodiments, one revolution of the drive member 820 or 821 may cause the actuating rod 804 to translate by a distance in the range of from about 9 mm to about 12 mm. In some embodiments, one revolution of the driver member 820 or 821 may generally approximate the estimated growth of a spine over a particular period, such as three months or six months. Overall, the length of the assembly 800, as measured from a distal-most end 805 of the actuating rod 804 to a distal-most end 807 of the fixed rod 806, may be configured to vary by an amount in the range of from about 5 cm to about 10 cm. For example, the assembly 800 may be configured to lengthen or extend by at least 7 cm. In yet other embodiments, the length of the assembly 800 may be configured to increase by a factor in the range of from about 10% to about 50%. In other embodiments, the length of the assembly 800 may be configured to increase by a factor in the range of from about 20% to about 30%. In yet other embodiments, the length of the assembly 800 may be configured to increase by about 25%.

Any drivers known in the art may be used to drive or rotate the drive member 820 or 821. In some embodiments, the driver may be actuated by a motor that may be coupled to a computer system or other electronics. In these embodiments, the driver may be incorporated into the assembly 800 (e.g., mounted in or on the elongate sleeve 802) or may be reversibly coupled with the assembly 800. In other embodiments, the driver, and consequently, the gear assembly 824, may be configured to be actuated manually, e.g., by hand. In these embodiments, the gear assembly 824 may be configured such that the amount of torque that is required to rotate the drive member and extend the actuating rod 804, while also counteracting any compressive or distractive forces within a spinal column, is within the range of a reasonable manual output, e.g., from about 1 N·m to about 10 N·m. For example, the gear assembly described herein having a gear ratio of 4:1 may be configured to be actuated upon receiving an input of about 2.5 N·m of torque. The gear assembly described herein having a gear ratio of 2:1 may be configured to be actuated upon receiving an input of about 5 N·m of torque. Those skilled in the art may appreciate that other gear sizes, combinations, and/or ratios may be utilized to vary the rate at which the assembly 800 lengthens (e.g., the rate at which the actuating rod 804 translates) and/or the input force required per revolution.

In some embodiments, the gear assembly 824 may further include a locking member, which may be configured to prevent translation of the actuating rod in a proximal (e.g., inward) direction. The locking member may be a spring-loaded pawl. The locking member may be coupled to the input gear 826 or its axle, and may be configured to directly engage the smaller member of the compound gear 832 or the idler gear. The locking member may be coupled to a lever, wherein the lever may be configured to disengage the locking member. The lever may be configured to be actuated by a driver, and in some embodiments, can be accessed through the socket 830. In use, if the assembly 800 needs to be shortened or retracted, a driver can be inserted into the socket 830 to activate (e.g., depress) the lever, thereby releasing the locking member and allowing gear train to rotate in reverse such that the actuating rod translates into the elongate sleeve 802.

As illustrated in FIG. 6B, the actuating rod 804 may include a plurality of gear teeth 836 thereon. In some embodiments, the actuating rod 804 may include a toothed section and one or more smooth or non-toothed sections 838, as illustrated in FIG. 6D. The actuating rod 804 may be at least partially disposed within a portion of the conduit 808 of the elongate sleeve 802, e.g., the first end 810, and may extend in a first direction. Additionally, a portion of the actuating rod 804 may extend distally beyond the first end 810 of the conduit 808. The distal-most end of the assembly 800 may also be the distal-most end of the actuating rod 804. As illustrated in FIGS. 6A-D, the actuating rod 804 may be straight (e.g., may extend longitudinally along a straight line). In other embodiments, it may be a curved rod. The smooth or non-toothed section 838 may have a circular transverse cross-section and/or can include an elongate cylinder having a constant outer diameter. In other embodiments, it may have a different cross-sectional shape, such as triangular, square, rectangular, pentagonal, or hexagonal. In some embodiments, the actuating rod 804 can be solid. In other embodiments, the actuating rod 804 can be hollow (e.g., can include a cannula or other passageway extending at least partially therethrough). The diameter of the actuating rod 804 can vary, and may be, for example, in the range of from about 3 mm to about 10 mm. In some embodiments, the diameter of the actuating rod 804 can be in the range of from about 4 mm to about 7 mm. As described herein, the gear assembly 824 may be configured to engage the actuating rod 804. In some embodiments, the gear assembly 824 and the actuating rod 804 may be configured for direct engagement, e.g., meshing the teeth on the output gear 828 and the teeth 836 on the actuating rod 804. As described herein, the actuating rod 804 may be held within the conduit 808 by one or more guide members (e.g., guide member 819).

Those skilled in the art may appreciate that the actuating rod 804 may be configured to slide and/or translate longitudinally within the elongate sleeve 802. Accordingly, the extendable rod assembly 800 can be configured to transition from a first configuration, wherein the assembly 800 is retracted, collapsed, shortened, un-expanded, and/or un-extended, as illustrated in FIGS. 6A-C, and a second configuration, wherein the assembly 800 is lengthened, expanded, and/or extended, as illustrated in FIG. 5D. In the first configuration, a proximal end of the actuating rod 804 can contact or be adjacent to a proximal end of the fixed rod 806 and an overall length of the assembly 800 may be minimized. In the second configuration, the proximal end of the actuating rod 804 may reach the first end 810 of the elongate sleeve 802 and the overall length of the assembly 800 may be maximized. In some embodiments, the assembly 800 may have a length in the range of from about 20 cm to about 25 cm when in the first configuration and a length in the range of from about 27 cm to about 32 cm when in the second configuration. Those skilled in the art may appreciate that the assembly 800 may also be capable of numerous intermediate configurations, wherein the overall length of the assembly 800 is greater than the fully retracted length and less than the fully extended length.

As illustrated in FIGS. 6A and 6D, the fixed rod 806 may include a cylinder having a circular transverse cross-section and/or a constant outer diameter. The fixed rod 806 may be at least partially disposed within the second end 812 of the conduit 808 and may extend in a second direction, e.g., opposite to that of the actuating rod 804. Additionally, a portion of the fixed rod 806 may extend distally beyond the second end 812 of the conduit 808. The fixed rod 806 may be held or secured within the conduit 808 by one or more guide members (e.g., guide member 819). The fixed rod 806 may be straight (e.g., may extend longitudinally along a straight line). In other embodiments, it may be curved. The fixed rod 806 may have a circular transverse cross-section. In other embodiments, the fixed rod 806 may have a different cross-sectional shape, such as triangular, square, rectangular, pentagonal, or hexagonal. In some embodiments, the fixed rod 806 may be solid. In other embodiments, the fixed rod 806 may be hollow (e.g., can include a cannula or other passageway extending at least partially therethrough). In some embodiments, the fixed rod 806 can include an elongate cylinder having a constant outer diameter. The diameter of the fixed rod 806 can vary, and may be, for example, in the range of from about 3 mm to about 10 mm. In some embodiments, the diameter of the fixed rod 806 can be in the range of from about 5 mm to about 7 mm. In other embodiments, the outer diameter of the fixed rod 806 can be the same as the outer diameter of the actuating rod 804. Those skilled in the art may appreciate that in other embodiments, the fixed rod 806 may be configured to translate, e.g., by adding gear teeth thereon that are accessible by a gear assembly, such that the assembly 800 can extend or elongate from both ends.

Embodiments herein are also directed to methods of extending the extendable rod assembly 800. In use, the extendable rod assembly 800 may be provided in a retracted, collapsed, shortened, and/or un-extended configuration having a first length, as illustrated, for example, in FIG. 6A. In embodiments where the extendable rod assembly 800 is being used to treat EOS, the extendable rod assembly 800 may be installed along a spine in the retracted configuration as described with respect to other extendable rod assemblies disclosed herein.

The method of extending the extendable rod assembly 800 may then include coupling a driver with the drive member 820 or 821. As described herein, any driver known in the art and configured to engage and apply torque to the drive member may be used. For example, in some embodiments the driver can include a wrench member, such as an Allen wrench or hex key, or a socket wrench member, such as a hex socket wrench. The method may then include applying torque to the drive member 820 or 821 in a first direction (e.g., clockwise). As illustrated in FIG. 6B, as the drive member turns clockwise, it can engage the input gear 826, which can also turn clockwise. This may cause the compound gear 832 (or idler gear) to turn counterclockwise and engage the output gear 828. This may cause the output gear 828 to turn clockwise, thereby engaging the teeth 836 on the actuating rod 804 and pushing the actuating rod 804 distally (e.g., out of the elongate sleeve 802). As described herein, the gear assembly 824 may advantageously be configured so that one revolution of the drive member 820 or 821 results in a lengthening of the extendable rod assembly 800 by an amount in the range of 5 mm to 10 mm. The locking member may prevent the actuating rod 804 from retracting back into the conduit 808 or 809. However, if the assembly 800 needs to be shortened, it may be reduced by disengaging the locking member and applying torque to the drive member in a second, opposite direction (e.g., counterclockwise). In use, a driver, which may be the same or different driver used to extend the assembly 800, may push the drive member 820 or 821 into the socket 830 of the input gear 826 until it engages the latch, thereby disengaging the locking member from the compound gear 832 (or idler gear). Once the locking member is disengaged, the driver may rotate the drive member 820 or 821 in a counterclockwise direction, which can thereby cause the actuating rod 804 to retract proximally into the conduit 808 or 809.

In some embodiments, the extendable or growing rods described above can be used with various other spinal implants, including but not limited to fusion devices and prosthetic devices. Fusion devices include cages, spacers (expandable and non-expandable), biological material (e.g., graft material inserted into the cages and spacers), corpectomy devices, plates, rod members and various fixation devices, including pedicle screws and hooks. Prosthetic devices include artificial discs, facet joint replacements, and any other implant that mimics anatomical motion.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. An extendable rod assembly configured to be implanted on a spine, comprising:
   an elongate sleeve comprising a first end and a second end and a second chamber extending therethrough;
   an actuating rod at least partially disposed within the elongate sleeve and extending in a first direction, the actuating rod comprising a first chamber;
   a valve assembly disposed within at least one of the actuating rod and the elongate sleeve, the valve assembly comprising a conduit, a cavity, a valve body, a stem, and a base; and
   a fixed rod at least partially disposed within the elongate sleeve and extending in a second direction, wherein the valve assembly regulates the flow of fluid between the second and first chambers, and wherein the stem is configured to automatically allow fluid to pass between the cavity and the conduit when a force is exerted on the valve body compressing the base due to growth of the spine.

2. The extendable rod assembly of claim 1, wherein the valve assembly comprises a hydraulic actuation mechanism.

3. The extendable rod assembly of claim 1, wherein the valve assembly comprises a pneumatic actuation mechanism.

4. The extendable rod assembly of claim 1, wherein the valve assembly comprises an automatic valve that regulates flow in response to changes in fluid pressure between the second chamber and the first chamber.

5. The extendable rod assembly of claim 1, wherein the valve assembly is a needle valve assembly.

6. The extendable rod assembly of claim 1, wherein the elongate sleeve comprises a first end cap at the first end and a second end cap at the second end.

7. The extendable rod assembly of claim 6, wherein first end cap has an opening to receive a portion of the actuating rod and the second end cap has an opening to receive a portion of the fixed rod.

8. The extendable rod assembly of claim 7, wherein the diameters of the openings in the first and second end caps are smaller than the diameter of the second chamber.

9. The extendable rod assembly of claim 8, wherein the actuating rod has an end portion with a diameter that is larger than the opening in the first end cap to prevent the actuating rod from disengaging from the elongate sleeve.

10. The extendable rod assembly of claim 8, wherein the fixed rod has an end portion with a diameter that is larger than the opening in the second end cap to prevent the fixed rod from disengaging from the elongate sleeve.

11. The extendable rod assembly of claim 6, wherein the first end cap and the second end cap are threadingly connected to the elongate sleeve.

12. The extendable rod assembly of claim 1, wherein the actuating rod is capable of translating with respect to the elongate sleeve and the fixed rod is not capable of translating with respect to the elongate sleeve.

13. An extendable rod assembly for a spine, comprising:
an elongate sleeve having a first end and a second end and comprising a first chamber extending between the first end and the second end;

a valve assembly moveably mounted in the elongate sleeve, wherein the valve assembly comprises a stem, a valve body, and a base;

an actuating rod at least partially disposed within the chamber and extending in a first direction, the actuating rod having a second chamber; and a fixed rod at least partially disposed within the chamber and extending in a second direction;

wherein the valve assembly fluidly connects the first chamber and the second chamber, and wherein the stem is configured to automatically allow fluid to pass between the first chamber and the second chamber when a force is exerted on the valve body compressing the base due to growth of the spine.

14. The extendable rod assembly of claim 13, wherein the valve assembly comprises a conduit and a cavity.

15. The extendable rod assembly of claim 13, wherein the valve assembly is a needle valve assembly.

16. The extendable rod assembly of claim 13, wherein the valve assembly comprises an automatic valve that regulates flow in response to changes in fluid pressure between the second chamber and the first chamber.

17. An extendable rod assembly for a spine, comprising:
an elongate sleeve comprising a chamber extending therethrough from a first end to a second end;

an actuating rod at least partially disposed within the first end of the chamber;

a fixed rod at least partially disposed within the second end of the chamber; and a valve assembly configured to actuate the actuating rod, wherein the valve assembly comprises a stem, a valve body, and a base, and wherein the stem is configured to automatically allow fluid to pass between the first chamber and the second chamber when a force is exerted on the valve body compressing the base due to growth of the spine.

18. The extendable rod assembly of claim 17, wherein the assembly is non-ferromagnetic.

19. The extendable rod assembly of claim 18, wherein the elongate sleeve comprises at least one guide member disposed within the chamber.

20. The extendable rod assembly of claim 19, wherein the guide member comprises a channel configured to receive the actuating rod therethrough.

* * * * *